United States Patent
Reicher

(10) Patent No.: US 11,205,515 B2
(45) Date of Patent: Dec. 21, 2021

(54) ANNOTATION AND ASSESSMENT OF IMAGES

(71) Applicant: INTERNATIONAL BUSINESS MACHINES CORPORATION, Armonk, NY (US)

(72) Inventor: Murray A. Reicher, Rancho Santa Fe, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/163,316

(22) Filed: May 24, 2016

(65) Prior Publication Data

US 2017/0046498 A1 Feb. 16, 2017

Related U.S. Application Data

(62) Division of application No. 13/300,239, filed on Nov. 18, 2011, now Pat. No. 9,378,331.

(Continued)

(51) Int. Cl.
| | |
|---|---|
| *G16H 50/20* | (2018.01) |
| *G16H 40/63* | (2018.01) |
| *G16H 50/50* | (2018.01) |
| *G16H 15/00* | (2018.01) |
| *G16H 30/40* | (2018.01) |
| *G06T 7/00* | (2017.01) |

(Continued)

(52) U.S. Cl.
CPC ......... *G16H 50/20* (2018.01); *G01R 33/4812* (2013.01); *G06T 7/0016* (2013.01); *G06T 11/60* (2013.01); *G16H 15/00* (2018.01); *G16H 30/40* (2018.01); *G16H 40/63* (2018.01); *G16H 50/50* (2018.01); *G06T 2207/20104* (2013.01); *G06T 2207/30096* (2013.01); *G09G 2380/08* (2013.01); *G16H 20/40* (2018.01)

(58) Field of Classification Search
CPC combination set(s) only.
See application file for complete search history.

(56) References Cited

U.S. PATENT DOCUMENTS

| | | | | |
|---|---|---|---|---|
| 6,081,612 | A | * | 6/2000 | Gutkowicz-Krusin ...................... A61B 5/0071 382/128 |
| 7,672,495 | B2 | * | 3/2010 | Evertsz ................. G06F 19/321 382/128 |

(Continued)

OTHER PUBLICATIONS

Eisenhauer et al., ("New response evaluation criteria in solid tumours: Revised RECIST guideline (version 1.1)". European Journal of Cancer 45 (2009); pp. 228-247. (Year: 2009).*

(Continued)

*Primary Examiner* — James M Kish
(74) *Attorney, Agent, or Firm* — Michael Best & Friedrich LLP

(57) ABSTRACT

Annotations of medical images may be generated using one or more lexicons so that terminology is consistent across multiple exams, users, facilities, etc. Measurements of lesions may be provided using a bilinear measurement tool that allows easier bilinear measurements. Disease assessment models may be selected and applied as measurements are acquired in order to provide immediate determination of disease staging according to one or more selected assessment models.

17 Claims, 18 Drawing Sheets

Related U.S. Application Data

(60) Provisional application No. 61/415,679, filed on Nov. 19, 2010.

(51) Int. Cl.
*G01R 33/48* (2006.01)
*G06T 11/60* (2006.01)
*G16H 20/40* (2018.01)

(56) References Cited

U.S. PATENT DOCUMENTS

| | | | |
|---|---|---|---|
| 7,894,646 B2 | 2/2011 | Shirahata | |
| 8,094,901 B1 | 1/2012 | Reicher et al. | |
| 9,378,331 B2 | 6/2016 | Reicher et al. | |
| 2001/0043729 A1 | 11/2001 | Giger | |
| 2002/0028006 A1 | 3/2002 | Novak | |
| 2002/0065460 A1 | 5/2002 | Murao | |
| 2002/0065466 A1* | 5/2002 | Rather | A61B 8/08 600/447 |
| 2003/0016850 A1 | 1/2003 | Kaufmann | |
| 2005/0147284 A1 | 7/2005 | Vining | |
| 2006/0034521 A1 | 2/2006 | Lindmark | |
| 2006/0063999 A1* | 3/2006 | Herron | A61N 5/1049 600/407 |
| 2006/0061595 A1 | 5/2006 | Goede | |
| 2006/0093198 A1 | 5/2006 | Fram et al. | |
| 2006/0095423 A1 | 5/2006 | Reicher et al. | |
| 2006/0106642 A1* | 5/2006 | Reicher | G06F 19/321 705/2 |
| 2007/0106633 A1 | 5/2007 | Reiner | |
| 2007/0168223 A1* | 7/2007 | Fors | G06F 19/324 705/2 |
| 2008/0037852 A1* | 2/2008 | Zhou | G06T 7/0012 382/132 |
| 2008/0201174 A1* | 8/2008 | Ramasubramanian | G16H 20/10 705/3 |
| 2008/0228061 A1* | 9/2008 | Habets | G06T 7/62 600/407 |
| 2009/0076379 A1 | 3/2009 | Hamill | |
| 2009/0182577 A1 | 7/2009 | Squilla et al. | |
| 2009/0213034 A1 | 8/2009 | Wu et al. | |
| 2010/0156898 A1* | 6/2010 | Voros | A61B 5/02007 345/419 |
| 2010/0226550 A1* | 9/2010 | Miyasa | G06F 19/321 382/128 |
| 2010/0254584 A1* | 10/2010 | Gulsun | A61B 5/055 382/131 |
| 2010/0284590 A1 | 11/2010 | Peng | |
| 2010/0293164 A1 | 11/2010 | Weese | |
| 2011/0145693 A1 | 6/2011 | Mutic | |
| 2011/0170755 A1 | 7/2011 | Buelow | |
| 2011/0182493 A1 | 7/2011 | Huber | |
| 2011/0243402 A1 | 11/2011 | Kadir | |
| 2011/0295118 A1 | 12/2011 | Okamura | |
| 2012/0008838 A1* | 1/2012 | Guyon | G06F 19/345 382/128 |
| 2012/0154431 A1 | 6/2012 | Fram | |
| 2017/0200064 A1 | 7/2017 | Reicher | |
| 2017/0200269 A1 | 7/2017 | Reicher et al. | |

OTHER PUBLICATIONS

Ecog, "Recist 1.1 Training Workshop". PowerPopint slides, 121 slides, https://federated.kb.wisc.edu/images/group150/41214/Fall12_RECIST_1.1(1).pdf (Year: 2012).*
Gottlieb et al., "Semiquantitative Visual Approach to Scoring Lung Cancer Treatment Response Using Computed Tomography: A Pilot Study", J Comput Assist Tomogr 2009;33: 743-747 (Year: 2009).*
Zhengping et al., "User-Preference-Based Service Selection Using Fuzzy Logic", 2010 International Conference on Network and Service Management—CNSM 2010: Short Papers, pp. 342-345. (Year: 2010).*
U.S. Appl. No. 14/818,167, Systems and User Interfaces for Automated Generation of Matching 2D Series of Medical Images and Efficient Annotation of Matching 2D Medical Images, filed Aug. 4, 2015.
AGFA HealthCare, color brochure "IMPAX 6: Digital Image and Information Management," © 2012 Agfa HealthCare N.V. Downloaded from http://www.agrahealthcare.com/globel/en/he/library/libraryopen?ID=32882925. Accessed on Feb. 9, 2015.
AGFA HealthCare, IMPAX 6.5 Datasheet (US)2012. © 2012 Agfa Healthcare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASPYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS Voew Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdi. Accessed on Feb. 9, 2015.
CANDELiS, ImageGrid™: Image Management Appliance, 6 page color brochure. (AD-012 Rev. F 11/2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 06/12). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 05/14). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wo-content/uploads/2013/08/EXAM-PACS-BROCHURE-final-web.pdf. Accessed on Feb. 9, 2015.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.

(56) References Cited

OTHER PUBLICATIONS

FUJIFILM Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
ICRco, I See The Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imaqeanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#Iproducts-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS. 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
intelerad, InteleViewer, 2 page color borchure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Technology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
PHILIPS IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
PHILIPS, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft PACS Products, 2 colore page printout. Accessed at http://www.ramsoft.com/products/powerserver-pacs-overrview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutons/intergy/. Accessed on Feb. 9, 2015.
Sclmage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutons/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalimaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/imaging/OfficePACSPowerDigitalimaging/ssLINK/emea/1557/022268. Accessed on Feb. 9, 2015.
UltraRAD—ultra VISION, 1 page (color). Downloaded from http://www.ultraradcorp.com/pdf/UltraViSION.pdf. Accessed on Feb. 9, 2015.
VioStream for VitreaView, 2 color pages printout. Accessed at http://www.vitalimages.com/solutions/universal-viewing/viostream-for-vitresview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Schellingerhout et al. "Coregistration of Head CT Comparision Studies: Assessment of Clinical Utility." Academic Radiology, vol. 10, No. 3. Mar. 2003. pp. 242-248.

(56) References Cited

OTHER PUBLICATIONS

Erickson et al. "Image Registration Improves Confidence and Accuracy of Image Interpretation." Cancer Informatics 2007: | 19-24.
Erickson et al. "Effect of Automated Image Registration on Radiologist Interpretation." Journal of Digital Imaging, vol. 20, No. 2 June. 2007; pp. 105-113.
Office Action dated Nov. 30, 2017, in U.S. Appl. No. 14/818,167.
United States Patent Office Action for U.S. Appl. No. 13/300,239 dated Jun. 10, 2013 (7 pages).
United States Patent Office Action for U.S. Appl. No. 13/300,239 dated Aug. 15, 2013 (14 pages).
United States Patent Office Action for U.S. Appl. No. 13/300,239 dated Aug. 14, 2014 (12 pages).
United States Patent Office Applicant Initiated Interview Summary for U.S. Appl. No. 13/300,239 dated Nov. 18, 2014.
United States Patent Office Notice of Allowance for U.S. Appl. No. 13/300,239 dated Jan. 16, 2015 (17 pages).
United States Patent Office Notice of Allowance for U.S. Appl. No. 13/300,239 dated Feb. 29, 2016 (7 pages).
United States Patent Office Action for U.S. Appl. No. 14/818,167 dated Nov. 30, 2017 (17 pages).
United States Patent Office Notice of Allowance for U.S. Appl. No. 14/818,167 dated May 9, 2018 (7 pages).
United States Patent Office Notice of Allowance for U.S. Appl. No. 14/818,167 dated May 23, 2018 (4 pages).
United States Patent Office Notice of Allowance for U.S. Appl. No. 14/818,167 dated Jul. 3, 2018 (9 pages).
May 24, 2016, U.S. Appl. No. 15/163,316, now U.S. Pat. No. 2017/0046498.
Nov. 18, 2011, U.S. Appl. No. 13/300,239, now U.S. Pat. No. 9,378,331.
Aug. 4, 2015, U.S. Appl. No. 14/818,167, now U.S. Pat. No. 10,127,662.

* cited by examiner

Record Annotation Data

Annotation type: Bidimensional

1. Select category:
- Anatomy
- Vessel
- Mass
- Node
- Implant

Organ Name:
- Abdomen
- Abdominal wall
- Adnexa
- Adrenal
- Appendix
- Axilla
- Auditory-external canal
- Auditory-internal canal
- Auditory-middle ear
- Auditory-ossicles
- Auditory-mastoid
- Biliary
- Bladder
- Bone
- ⊞ Brain
- Cardiac
- Cervix
- Chest
- Chest wall
- ⊞ Colon
- Dental Measured value: 3.38 cm x 2.65 cm

Index Lesion #:
- Index lesion #1
- Index lesion #2
- Index lesion #3
- Index lesion #4
- Index lesion #5
- Index lesion #6
- Index lesion #7
- Index lesion #8
- Index lesion #9
- Index lesion #10
- Index lesion #11
- Index lesion #12
- Index lesion #13
- Index lesion #14
- Index lesion #15
- Index lesion #16
- Index lesion #17
- Index lesion #18
- Index lesion #19
- Index lesion #20

Position: [Add]
- Right
- Anterior
- Capsular
- Deep
- Diffuse
- Distal
- Inferior
- Lateral
- Left
- Lower pole
- Medial
- Mid
- Mid-pole
- Posterior
- Proximal
- Right
- Subcapsular
- Superficial
- Superior
- Upper pole

Mass Type: [Add]
- Benign-appearing
- Complex cyst
- Metastasis
- Necrotic-appearing
- Primary Tumor
- Probable metastasis
- Probable primary tumor
- Simple cyst
- Solid

Characteristics: [Add]
- Cold nodule
- Containing calcifications
- Decreased uptake
- Densely calcified
- FDG-avid
- Hemorrhagic
- High signal intensity
- Hot nodule
- Hyperechoic
- Hypervascular
- Hypoechoic
- Hypovascular
- Increased uptake
- Isointense
- Low signal intensity
- Rim-calcified

Histology: [Add]
- Angiosarcoma
- Astrocytoma
- Basal cell carcinoma
- Bronchial adenoma
- Bronchogenic carcinoma
- Carcinoma
- Cholangiocarcinoma
- Chondrosarcoma
- Chordoma
- DCIS
- Embryonal carcinoma
- Enchondroma
- Ependymoma
- Epidermoid
- Ewing sarcoma
- Fibroma
- Fibrosarcoma
- Fibrous dysplasia
- Ganglioglioma
- Giant cell tumor
- Glioblastoma
- Hemangioblastoma
- Hemangioma
- Hepatoma

Annotation label: Index lesion #1: auditory-internal canal, right, acoustic neuroma (3.38 cm x 2.65 cm).

[OK] [Cancel]

Annotation Data – Assessment Criteria View

| | | |
|---|---|---|
| Exam Date | Annotation Data | Measurement |
| 10/10/2006 | Index Lesion #1 | (3.38 cm x 2.65 cm) |
| | Index Lesion #2 | (1.81 cm x 0.32 cm) |
| | Index Lesion #3 | (0.84 cm x 1.42 cm) |
| | Assessment Score | (Baseline) LD = 6.61 |
| | | |
| Exam Date | Annotation Data | Measurement |
| 11/5/2006 | Index Lesion #1 | (4.48 cm x 2.95 cm) |
| | Index Lesion #2 | (2.51 cm x 1.01 cm) |
| | Index Lesion #3 | (1.76 cm x 1.99 cm) |
| | Assessment Score | LD = 8.98 (+35%) PD |
| | | |
| Exam Date | Annotation Data | Measurement |
| 1/2/2007 | Index Lesion #1 | (4.08 cm x 2.65 cm) |
| | Index Lesion #2 | (2.11 cm x 0.61 cm) |
| | Index Lesion #3 | (1.36 cm x 1.29 cm) |
| | Assessment Score | LD = 7.55 (−16%) SD |

Treatment Dates

11/7/2006 Chemo Round 1 (Treatment 1)
11/14/2006 Chemo Round 1 (Treatment 2)
11/21/2006 Chemo Round 2 (Treatment 1)
12/2/2006 Chemo Round 2 (Treatment 2)
12/16/2006 Chemo Round 3 (Treatment 1)
12/30/2006 Chemo Round 3 (Treatment 2)

1/14/2007 Radiation Treatment 1 planned

[Toggle SA Scores] [Scoring Model] [DR 0.1]

[Copy Text to Report] [Copy Text to Clipboard] [Done]

| COMPARISON: | MR. BRAIN WO W. Oct-13-05.07:33. |
|---|---|
| INDICATIONS: | Headache. History of meningioma status post gamma knife. |
| TECHNIQUE: | A variety of imaging planes and parameters were utilized for visualization of suspected pathology. Images were performed without and with gadolininum contrast. |

FINDINGS:

| CEREBRUM: | No edema, hemorrhage, mass, acute infarction, ot inappropriate atrophy. |
|---|---|
| CEREBELLUM: | No edema, hemorrhage, mass, acute infarction, ot inappropriate atrophy. |
| BRAINSTEM: | No edema, hemorrhage, mass, acute infarction, ot inappropriate atrophy. |
| CSF SPACES: | Mass in the right cerebellopontine angle cistern. Please see table below for measurements and comparison to prior exams. |
| SKULL: | No mass or other significant visible lesion. |
| SINUSES: | Limited views dermonstrate no significant mucosal thickening or fluid. |
| ORBITS: | Limited views are unremarkable. |
| OTHER: | No abnormal meningeal or parenchymal enhancement. |
| 10/10/2006 | Index lession #1 auditory-internal canal, right, acoustic neuroma (3.38 cm x 2 <5 cm). |
| 10/13/2005 | Index lession #1 auditory-internal canal, right, benign-appearing, acoustic neuroma (3.27 cm x 2.56 cm). |

CONCLUSION: WARNING: THIS REPORT WAS APPROVED PREMATURELY AND IS NOT ACCURATE. PLEASE CONTACT US IMMEDIATELY.

Dictated by: Murray A. Reicher, M.D.

ANNOTATION AND ASSESSMENT OF IMAGES

CROSS-REFERENCE TO RELATED APPLICATIONS

This application is a divisional of U.S. patent application Ser. No. 13/300,239, filed Nov. 18, 2011, and titled "ANNOTATION AND ASSESSMENT OF IMAGES," which application claims the benefit of priority under 35 U.S.C. § 119(e) of U.S. Provisional Application No. 61/415,679, filed Nov. 19, 2010, and titled "AUTOMATED LABELING." The entire disclosure of each of the above items is hereby made part of this specification as if set forth fully herein and incorporated by reference for all purposes, for all that it contains.

BACKGROUND

When a patient undergoes a medical imaging exam, it is common for the reading physician to make measurements or create annotations using computerized reading systems, commonly called PACS (picture archive and communication systems). Tumors, vascular stenosis, organs, or other items may be measured using linear dimensions, area, density in Hounsfield units, optical density, standard uptake value (for positron emission tomography), volume, curved lines (such as the length of a curved vessel), stenosis (percent narrowing of a vessel at a certain location relative to a reference location), or other parameters. In addition, annotations may include arrows to indicate specific locations or anatomy, circles, polygons, irregularly shaped areas, etc.

SUMMARY

For purposes of this summary, certain aspects, advantages, and novel features are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

In one embodiment, a computing system comprises one or more hardware processors configured to execute software instructions stored in modules and a tangible computer readable medium storing modules configured for execution by the one or more hardware processors. In one embodiment, the modules include a display module configured to display a medical image on a display of the computing system and an annotation module. In one embodiment, the annotation module is configured to provide a user interface on the display in response to completion of a measurement of a lesion on the medical image, the user interface including characteristics associated with the lesion that are selectable by the user, receive indications of one or more of the characteristics that are selected via the user interface, generate an annotation based on the one or more selected characteristics, wherein the user interface or another user interface allows the user to select a particular index of a plurality of indexes to associated with the lesion, wherein association of the lesion with the particular index allows the annotation module to associate the lesion with annotation data of the particular lesion in other exams, and store the generated annotation with an association to the medical image.

In one embodiment, a computing system comprises one or more hardware processors configured to execute software instructions stored in modules, and a tangible computer readable medium storing modules configured for execution by the one or more hardware processors. In one embodiment, the modules include a display module configured to display a medical image on a display of the computing system, and a bilinear measurement module. In one embodiment, the bilinear measurement module is configured to, in response to a predefined first input from an input device of the computing system, display a bilinear measurement tool on the medical image, the bilinear measurement tool having two axes that are independently adjustable to adjust respective lengths of the axes, in response to a predefined second input from an input device of the computing system, adjust a length of the first axis, in response to a predefined third input from an input device of the computing system, adjust a length of the second axis, and, determine a first length of the first axis and a second length of the second axis.

In one embodiment, a computing system comprises one or more hardware processors configured to execute software instructions stored in modules, and a tangible computer readable medium storing modules configured for execution by the one or more hardware processors. In one embodiment, the modules include an assessment module configured to determine an assessment model to apply in determining a disease stage of a patient, access rules of the determined assessment model, access lesion measurement data from two or more exams of the patient, select the lesion measurement data that satisfies the rules of the determined assessment model, determine a baseline assessment scores based on measurement data from one or more of the two or more exams of the patient, determine a current assessment scores based on measurement data from a latest exam of the patient, compare the baseline assessment scores with the current assessment scores in accordance with the determined assessment model, and determine a disease stage based on the comparison of the baseline assessment scores with the current assessment scores in accordance with the determined assessment model.

BRIEF DESCRIPTION OF THE DRAWINGS

As shown in FIG. 1, the computing system may be in communication with various other computing systems.

FIG. 5 is a sample user interface that may be used by the viewer to index the tumor that was annotated in FIGS. 3-4 through the selection of various descriptive terms.

FIG. 15 is a sample user interface that includes measurements for multiple index lesions at each of three different exam times.

FIG. 17 is a sample report that includes annotations that were recorded while viewing images and were automatically included (or via a copy and paste by the user) into the report.

These and other features will now be described with reference to the drawings summarized above. The drawings and the associated descriptions are provided to illustrate certain embodiments of the invention and not to limit the scope of the invention. Throughout the drawings, reference numbers may be re-used to indicate correspondence between referenced elements. In addition, the first digit of each reference number generally indicates the figure in which the element first appears.

DETAILED DESCRIPTION

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

As used herein, the terms "viewer" and "user" are used interchangeably to describe an individual (or group of individuals) that interfaces with a computing device, such as the computing system 150 discussed below. Users may include, for example, doctors, radiologists, hospital staff, or other individuals involved in acquisition, analysis, storage, management, or other tasks related to medical images. Any discussion herein of user preferences should be construed to also, or alternatively, include user group preferences, site preferences, system preferences, and/or default software preferences.

Depending on the embodiment, the methods described with reference to the flowcharts, as well as any other methods discussed herein, may include fewer or additional blocks and/or the blocks may be performed in a different order than is illustrated. Software code configured for execution on a computing device in order to perform the methods may be provided on a computer readable medium, such as a compact disc, digital video disc, flash drive, hard drive, memory device or any other tangible medium. Such software code may be stored, partially or fully, on a memory of a computing device (e.g., RAM, ROM, etc.), such as the computing system 150, and/or other computing devices illustrated in the figures, in order to perform the respective methods. For ease of explanation, the methods will be described herein as performed by the computing system 150, but the methods are not limited to performance by the computing system 150 and should be interpreted to include performance by any one or more of the computing devices noted herein and/or any other suitable computing device.

Example System Configuration

Figure 1:
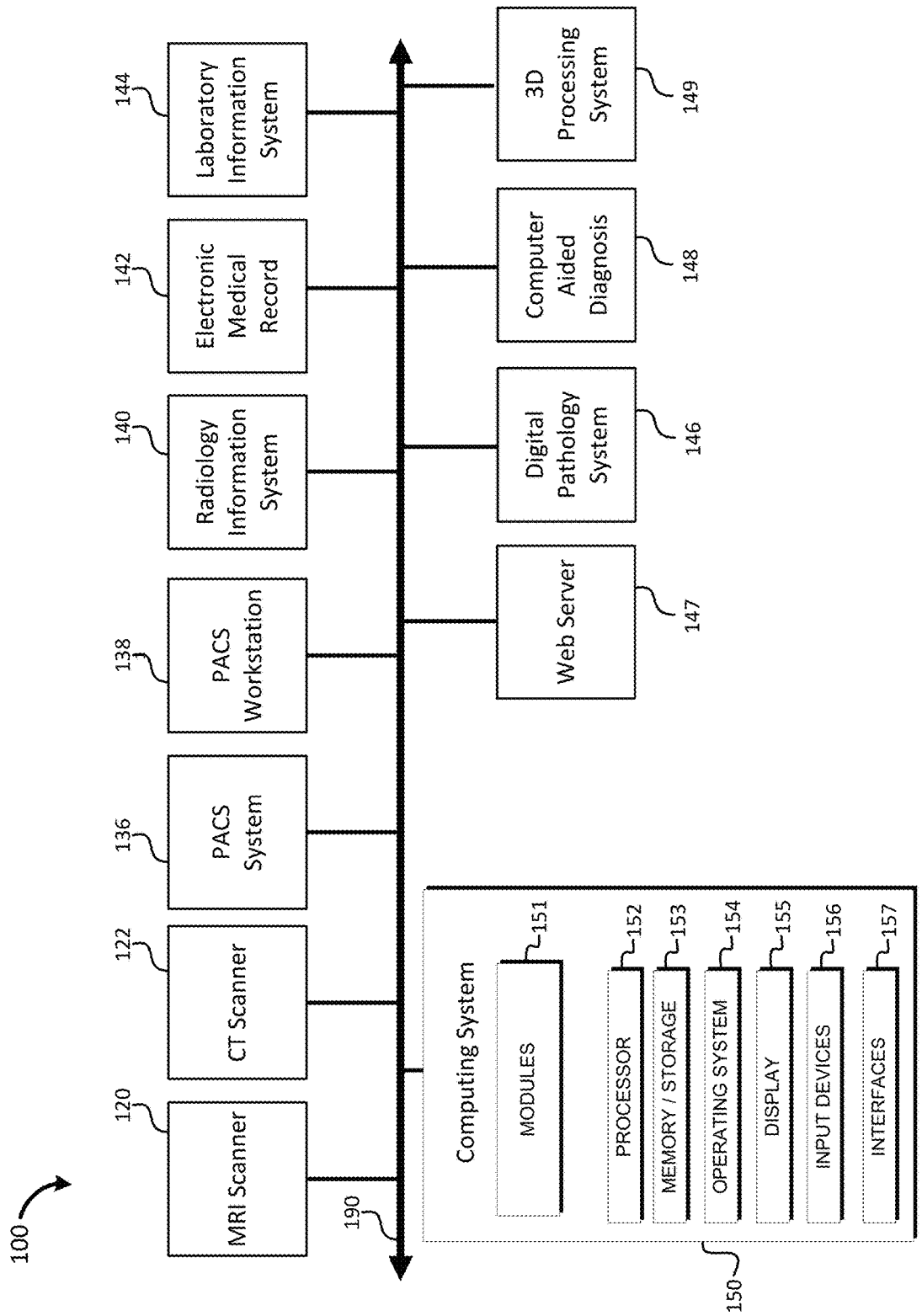
FIG. 1 is a block diagram illustrating a computing system that may perform the various methods and features discussed hereinafter.

FIG. 1 is a block diagram illustrating a computing system 150 that may perform the various methods and features discussed hereinafter. As shown in FIG. 1, the computing system 150 may be in communication with various other computing systems and/or components.

The computing system 150 may take various forms. In one embodiment, the computing system 150 may be a computer workstation having software modules 151 (described in further detail below). In other embodiments, software modules 151 may reside on another computing device, such as a web server, and the computing system 150 interacts with the another computing device via a computer network.

In one embodiment, the computing system 150 comprises one or more of a server, a desktop computer, a workstation, a laptop computer, a mobile computer, a smartphone, a tablet computer, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, for example. The computing system 150 may include multiple of the above-noted devices.

The computing system 150 may run an off-the-shelf operating system 154 such as a Windows, Linux, MacOS, Android, or iOS. The computing system 150 may also run a more specialized operating system which may be designed for the specific tasks performed by the computing system 150.

The computing system 150 may include one or more hardware computing processors 152. The computer processors 152 may include central processing units (CPUs), and may further include dedicated processors such as graphics processor chips, or other specialized processors. The processors generally are used to execute computer instructions of the software modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules 151 may include software code written in a programming language, such as, for example, Java, JavaScript, ActionScript, Visual Basic, HTML, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The computing system 150 may also include memory 153. The memory 153 may include volatile data storage such as RAM or SDRAM. The memory 153 may also include more permanent forms of storage such as a hard disk drive, a flash disk, flash memory, a solid state drive, or some other type of non-volatile storage.

The computing system 150 may also include or be interfaced to one or more display devices 155 that provide information to the users. Display devices 155 may include a video display, such as one or more high-resolution computer monitors, or a display device integrated into or attached to a laptop computer, handheld computer, smartphone, computer tablet device, or medical scanner. In other embodiments, the display device 155 may include an LCD, OLED, or other thin screen display surface, a monitor, television, projector, a display integrated into wearable glasses, or any other device that visually depicts user interfaces and data to viewers.

The computing system 150 may also include or be interfaced to one or more input devices 156 that receive input from users, such as a keyboard, trackball, mouse, 3D mouse, drawing tablet, joystick, game controller, touch screen (e.g., capacitive or resistive touch screen), touchpad, accelerometer, video camera and/or microphone.

The computing system 150 may also include one or more interfaces 157 that allow information exchange between computing system 150 and other computers and input/output devices using systems such as Ethernet, Wi-Fi, Bluetooth, as well as other wired and wireless data communications techniques.

The modules of the computing system 150 may be connected using a standard based bus system. In different embodiments, the standard based bus system could be Peripheral Component Interconnect ("PCI"), PCI Express, Accelerated Graphics Port ("AGP"), Micro channel, Small Computer System Interface ("SCSI"), Industrial Standard Architecture ("ISA") and Extended ISA ("EISA") architectures, for example. In addition, the functionality provided for in the components and modules of computing system 150 may be combined into fewer components and modules or further separated into additional components and modules.

The computing system 150 may communicate and/or interface with other systems and/or devices. In one or more embodiments, the computing system 150 may be connected to a computer network 190. The computer network 190 may take various forms. It may be a wired network or a wireless network, or it may be some combination of both. The computer network 190 may be a single computer network, or it may be a combination or collection of different networks and network protocols. For example, the computer network 190 may include one or more local area networks (LAN), wide area networks (WAN), personal area networks (PAN), cellular or data networks, and/or the Internet.

Various devices and subsystems may be connected to the network 190. For example, one or more medical scanners may be connected, such as MRI scanners 120. The MRI scanner 120 may be used to acquire MRI images of patients, and may share the acquired images with other devices on the network 190. The network 190 may also include one or more CT scanners 122. The CT scanners 122 may also be used to acquire images and, like the MRI scanner 120, may then store those images and/or share those images with other devices via the network 190. Any other scanner or device capable of inputting or generating information that can be displayed as images or text could be included, including ultrasound, angiography, nuclear medicine, radiography, endoscopy, pathology, dermatology, etc.

Also connected to the network 190 may be a Picture Archiving and Communications System (PACS) 136 and PACS workstation 138. The PACS 136 is typically used for the storage, retrieval, distribution and/or presentation of images (such as those created and/or generated by the MRI scanner 120 and CT Scanner 122). The medical images may be stored in an independent format, an open source format, or some other proprietary format. One format for image storage in the PACS system is the Digital Imaging and Communications in Medicine (DICOM) format. The stored images may be transmitted digitally via the PACS system, often reducing or eliminating the need for manually creating, filing, or transporting film jackets. In one embodiment, the computing system 150 comprises a PACS 136.

The network 190 may also be connected to a Radiology Information System (RIS) 140. The radiology information system 140 is typically a computerized data storage system that is used by radiology departments to store, manipulate and distribute patient radiological information.

Also attached to the network 190 may be an Electronic Medical Record (EMR) system 142. The EMR system 142 may be configured to store and make accessible to a plurality of medical practitioners computerized medical records. Also attached to the network 190 may be a Laboratory Information System 144. Laboratory Information System 144 is typically a software system which stores information created or generated by clinical laboratories. Also attached to the network 190 may be a Digital Pathology System 146 used to digitally manage and store information related to medical pathology.

Also attached to the network 190 may be a Computer Aided Diagnosis System (CAD) 148 used to analyze images. In one embodiment, the CAD 148 functionality may reside in a computing device separate from computing system 150 while in another embodiment the CAD 148 functionality may reside within computing system 150.

Also attached to the network 190 may be a 3D Processing System 149 used to perform computations on imaging information to create new views of the information, e.g., 3D volumetric display, Multiplanar Reconstruction (MPR) and Maximum Intensity Projection reconstruction (MIP). In one embodiment, the 3D Processing functionality may reside in a computing device separate from computing system 150 while in another embodiment the 3D Processing functionality may reside within computing system 150.

In other embodiments, other computing devices that store, provide, acquire, and/or otherwise manipulate medical data may also be coupled to the network 190 and may be in communication with one or more of the devices illustrated in FIG. 1, such as with the computing system 150.

Depending on the embodiment, the devices 120-149 illustrated in FIG. 1 may include some or all of the same components discussed above with reference to the computing system 150. For ease of discussion, the embodiments discussed herein are with reference to medical images; however, the systems and methods discussed may be applied to any type of image. Thus, any reference herein to a medical image could be alternatively construed to cover an image, in general, or any other type of specialized image.

Example Modules

In the embodiment of FIG. 1, the computing system 150 includes modules 151, which may include one or more modules configured for execution by the computing system 150. The modules discussed below as part of the modules 151 may be distributed across multiple devices, and may be controlled and/or operated by multiple different entities. In other embodiments, the computing system may include fewer and/or different modules than are discussed herein.

In one embodiment, the modules 151 include a bilinear measurement module that is configured to generate and coordinate operations of a bilinear measurement tool that allows the user of the computing system 150 to easily measure features of a medical image in two or more dimensions. The bilinear measurement tool is discussed below with reference to FIGS. 2A-2B. In one embodiment, the software modules 151 include an annotation module configured to receive annotation data from the user of the computing system 150 and to store the annotation data with the medical image. Various annotation recordation techniques and features are discussed, for example, with reference to FIGS. 3-17. In one embodiment, the software modules 151 include an assessment module configured to access data regarding one or more assessment models and apply the assessment models to measurement data of a current image and/or related images from the current and/or previous exams. Various methods performed by the assessment module are discussed and illustrated with reference to FIGS. 9-15, for example. In other embodiments, one or more of the above noted software modules, as well as other software modules may be implemented by the computing system 150 and/or other computing systems illustrated in FIG. 1.

Bilinear Measurement Tool

Figure 2A:
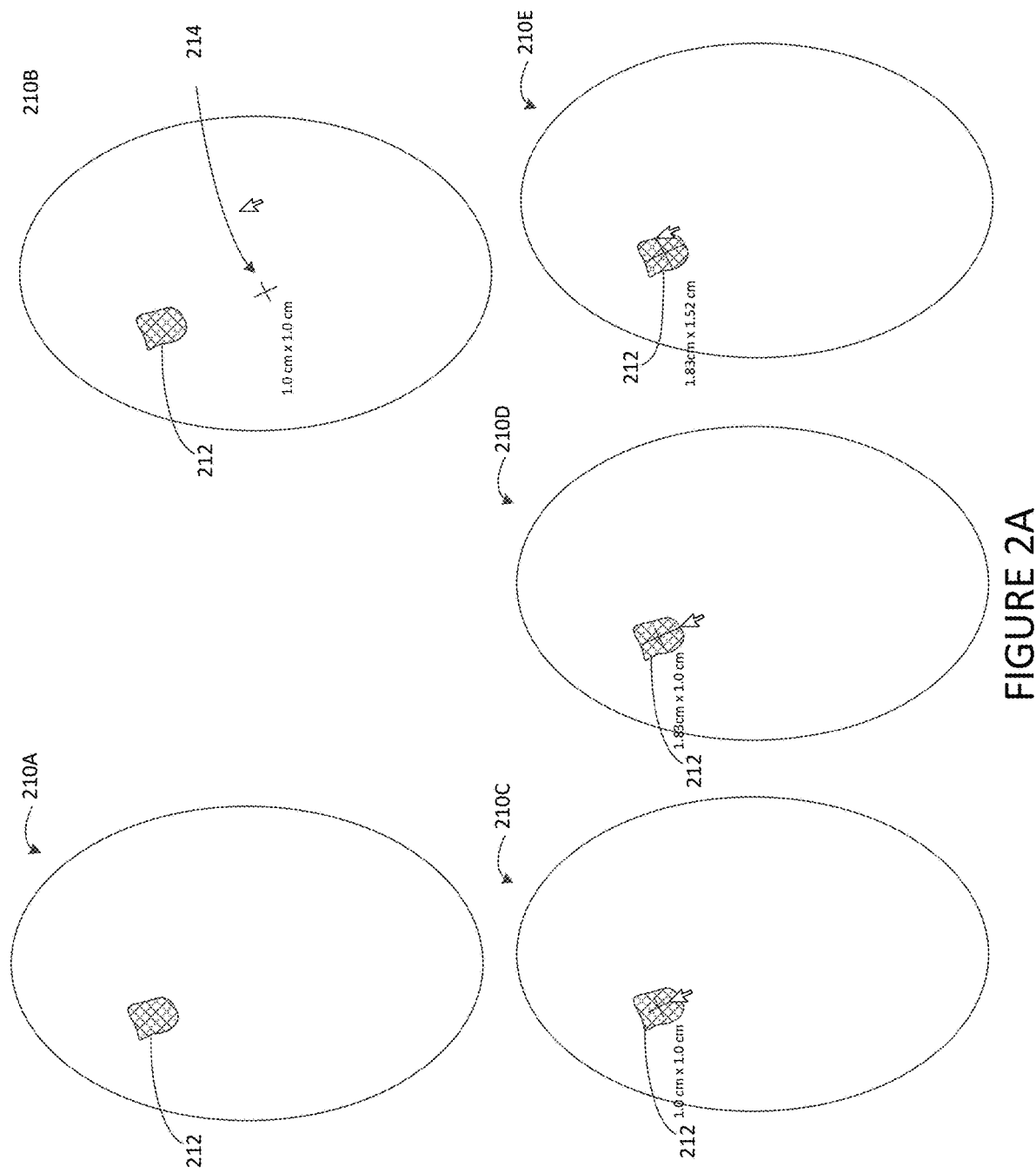
FIG. 2A is a diagram showing use of a bilinear measurement tool that allows easier bilinear measurements to be made.

FIG. 2A is a diagram showing use of a bilinear measurement tool that allows easier bilinear measurements to be made. In the embodiment of FIG. 2A, a user interface 210 (including 210A-210E) illustrating a representation of a medical image, such as a CT or MRI image of a brain, is shown over time as a bilinear measurement tool is used to measure a tumor in the image. In particular, the user interface 210 is shown at five times, in chronological order from 210A to 210E, to illustrate an example use of a bilinear measurement tool.

In user interface 210A, a tumor 212 (or any lesion or other item of interest to the viewer) is identified. In this embodiment, the viewer wishes to measure multiple dimensions of the tumor, such as a longest diameter and/or a short axis of the tumor 212. Rather than using a linear measurement tool multiple times, the user may select a bilinear measurement tool in order to more easily measure multiple dimensions of the tumor 212. Depending on the embodiment, the bilinear measurement tool may be selected in any manner, such as by selecting a menu option or icon, performing a keyboard (or other input device) shortcut, or providing input of any other form (e.g., a voice command). For example, in one embodiment the bilinear measurement tool is placed at the position of the cursor in response to selection on a pop-up menu (e.g., in response to a left-click) or in response to any other input.

The user interface 210B illustrates the same medical image and tumor 212, with a bilinear measurement tool 214 also placed on the image. In this embodiment, the bilinear measurement tool 214 has a default length that is equivalent in each dimension (both axes of the bilinear measurement tool 214 are equal length). However, the default length may be adjusted so that one axis of the measurement tool is longer than the other axis (e.g., so that the longer axis is used to measure the longest diameter of the tumor and the shorter axis of the tool is used to measure the short axis of the tumor). In one embodiment, the placement and/or size of the bilinear measurement tool is configurable based on user preference or characteristics of the images being viewed, as well as any other factors. For example, images of different modalities may be associated with default bilinear measurement tool sizes that are different.

The user interface 210C shows the bilinear measurement tool moved onto the tumor 212. For example, the bilinear measurement tool may be moved by clicking and dragging the tool using mouse, keyboard, or other input devices. In one embodiment, the bilinear measurement tool may be automatically positioned on lesions based on results of computer aided diagnostics that are performed on the medical image or user preferences. In another embodiment, the bilinear measurement tool is positioned at the same location as measurements were taken in a previous exam of the patient. Placement in this embodiment may be an absolute placement (e.g., the same pixel row and column of the image) or relative placement (e.g., the computing system 150, or other computing system, may determine an anatomical position of the previous measurement and place the bilinear measurement tool at the same anatomical position of the current medical image, regardless of the absolute pixel row and column of the images).

The user interface 210D shows a first axis of the bilinear measurement tool being adjusted, in this example to measure the longest diameter of tumor 212. The user interface 210E shows a second axis of the bilinear measurement tool being adjusted, in this example to measure the short axis of the tumor 212. In one embodiment, the bilinear measurement tool is rotatable, such as by selecting and dragging an outer edge of the tool, in order to place the axes at the proper orientation to make the most accurate measurement. In one embodiment, the axes are rotatable with reference to one another such that the angle between the two measurement axes is something different than 90 degrees. Additionally, in some embodiments more than two measurement axes may be included in a measurement tool, such as by default when the measurement tool is first placed in the user interface or by selection of an appropriate command by the user indicating that an additional measurement axis should be added.

Figure 2B:
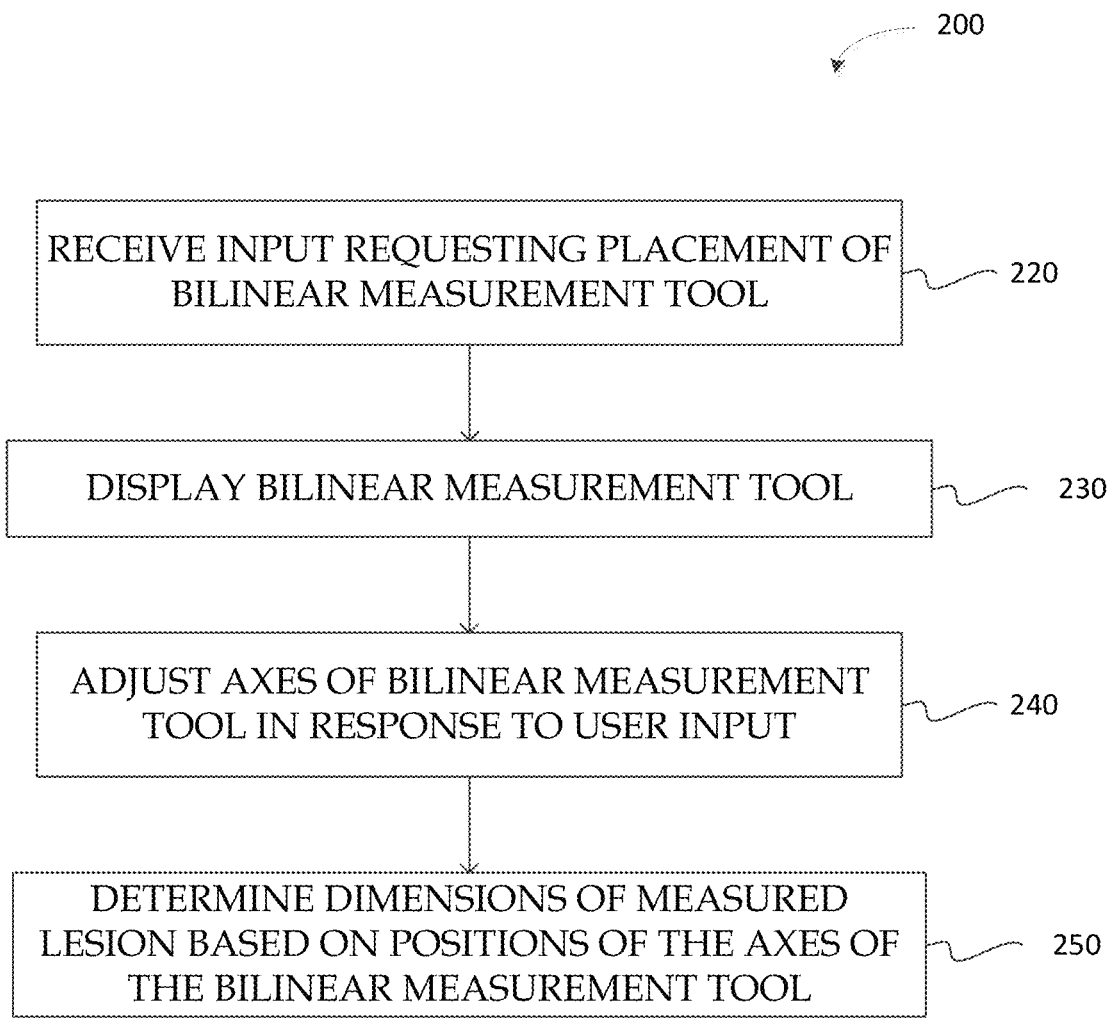
FIG. 2B is a flowchart illustrating one embodiment of a method of providing a bilinear measurement tool.

FIG. 2B is a flowchart illustrating one embodiment of a method of providing a bilinear measurement tool. Depending on the embodiment, the method of FIG. 2B may include fewer or additional blocks and/or the blocks may be performed in a different order than is illustrated. In one embodiment, the method of FIG. 2 is performed by the modules 151 of the computing system 150 and, more particularly, by the bilinear measurement module.

Beginning in block 220, the computing system 150 receives input from a user of the computing system 150 indicating that a bilinear measurement tool is desired, for example, to measure a lesion that is identified in the medical image. Depending on the embodiment, the input may come from one or more of any available input device, such as selection of a toolbar icon, a menu command, a keyboard shortcut, a mouse or touchpad command, a voice command, etc.

Next, in block 230, the computing system displays the bilinear measurement tool on the medical image. In one embodiment, the bilinear measurement tool is displayed at a default location, such as a center of the medical image. In other embodiments, the bilinear measurement tool may be displayed at locations that are customized based on characteristics of the medical image, the lesion, the user, the acquisition site, and/or any other characteristic related to the image. For example, the bilinear measurement module may access data associated with the medical image, such as DICOM header information, in order to determine that the bilinear measurement tool should be placed at a particular location of the medical image. In one embodiment, the bilinear measurement module has access to previous measurements of medical images associated with the same patient (or other patients). In this embodiment, the bilinear measurement module may access the measurement data and place the bilinear measurement tool at the same location as previous measurements were made in related images, for example. Thus, the bilinear measurement tool may be automatically placed on a lesion at a location that is determined by accessing previous measurements for the patient.

In block 240, the bilinear measurement module adjusts the axes of the bilinear measurement tool in response to user input. In one embodiment, the user input comprises clicking and dragging the ends of respective axes. In other embodiments, any other inputs from the user may be used to adjust the axes of the bilinear measurement tool. In one embodiment, each of axes is independently adjustable, such that the axes may be adjusted to different lengths. In one embodiment, the bilinear measurement module includes (or has access to) some computer aided diagnostic functionality that identifies the edges of a lesion on which the bilinear measurement tool is placed. In this embodiment, the axes of the bilinear measurement tool may be automatically adjusted (e.g., by the computing system 150 executing the bilinear measurement module) to measure the lesion in response to the bilinear measurement tool being placed on a particular lesion (either manually by the user moving the bilinear measurement tool, or automatically by one or more of the methods discussed above with reference to block 230, for example).

Next, in block 250, the bilinear measurement module determines measurements of the lesion based on the positions of the axes of the bilinear measurement tool. For example, a separate measurement may be acquired for each of the axes (e.g., a width and height measurement). In some embodiments, derived measurements may be calculated, such as an area measurement that is calculated based on the separate axis measurements. In one embodiment, the measurements are provided to the annotation module (discussed below) for inclusion in annotations and/or reports associated with the medical image and/or to the assessment module for use in determining disease classifications.

Annotations

Figure 3:
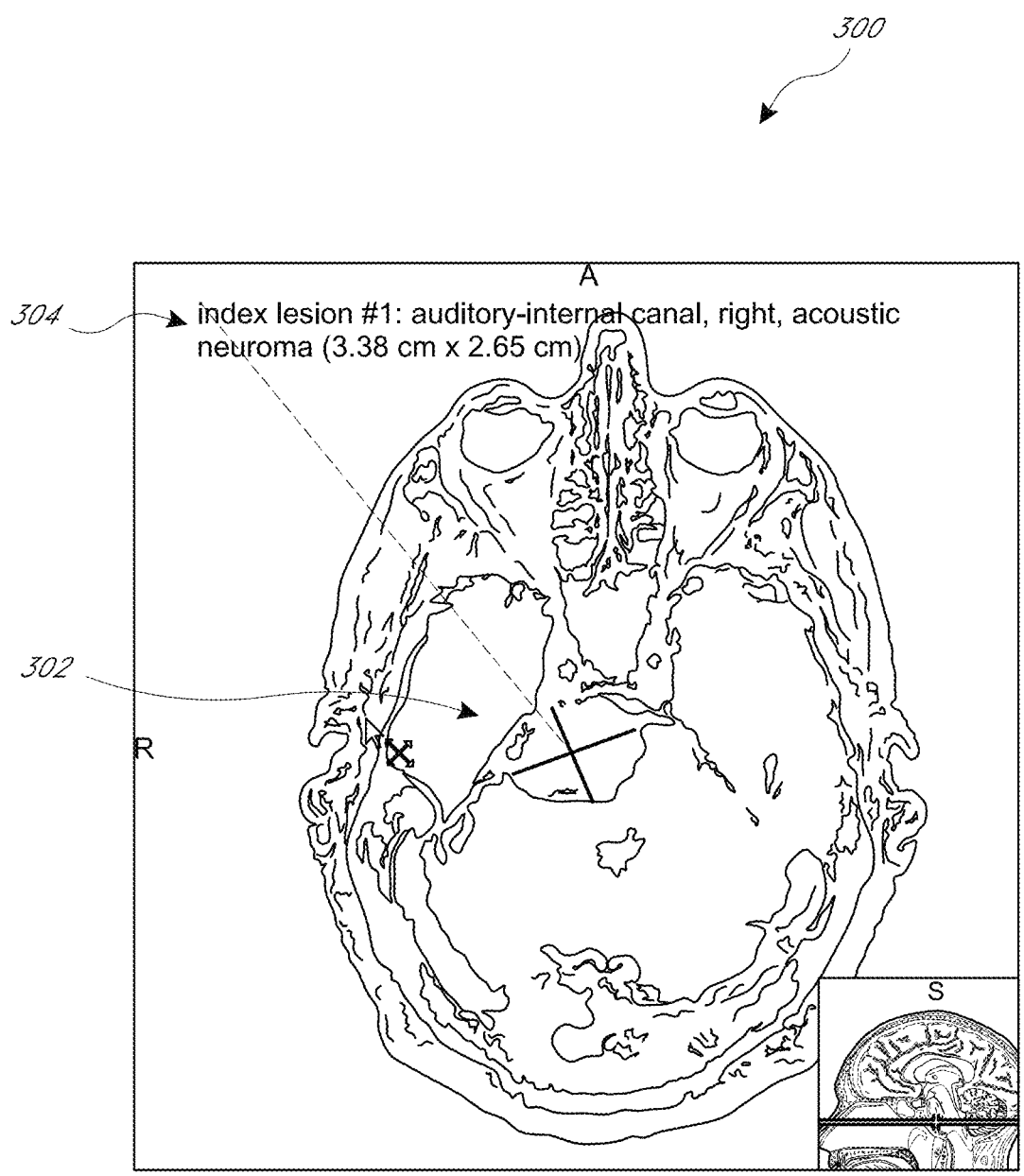
FIG. 3 is a sample user interface illustrating a medical image (e.g., an MRI image in this example), a measurement of a tumor in the medical image, and the addition of an annotation associated with the measurement.

FIG. 3 is a sample user interface 300 illustrating a medical image (e.g., an MRI image in this example), a measurement of a tumor 302 in the medical image, and an annotation 304 associated with the measurement. The annotation may be entered in response to a particular input (e.g., keyboard, mouse, etc.) from the user of the computing system 150, or may be requested in response to completion of a measurement. Advantageously, the current measurement (e.g., by the bilinear measurement tool illustrated over the tumor 302 in FIG. 3) may be automatically included in the annotation 304.

Figure 4:
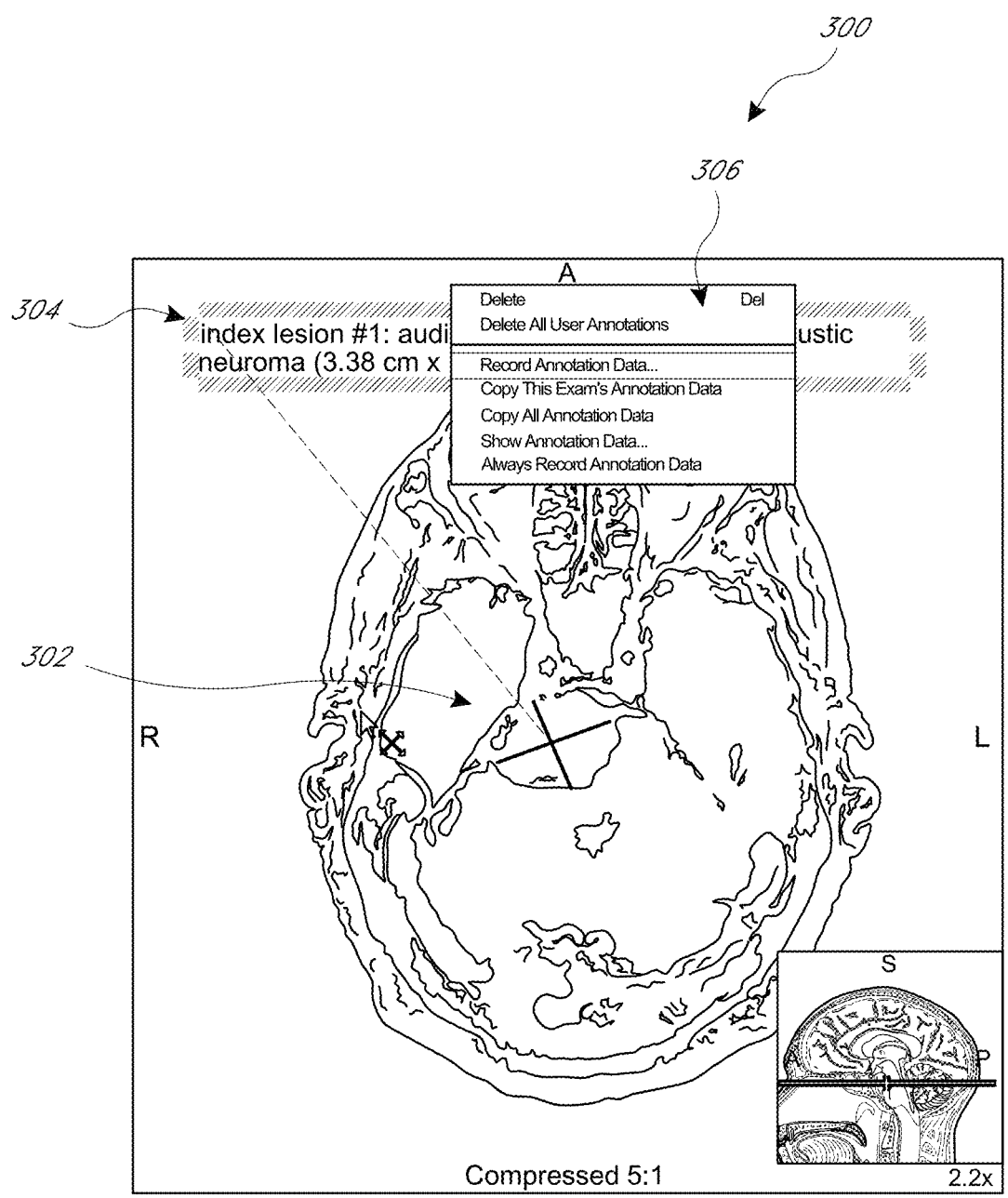
FIG. 4 is the sample user interface of FIG. 3, with a menu displayed that allows the user to indicate that the particular annotation, and other accompanying data, such as measurement data, should be stored with the image and made available to subsequent viewers that view related images.

FIG. 4 is the sample user interface 300 of FIG. 3, with a menu 306 displayed that allows the user to indicate that the particular annotation, and other accompanying data, such as measurement data, should be stored with the image and made available to subsequent viewers that view related images (e.g., images of the same patient and same anatomy). As discussed in further detail herein, annotation data, measurement data, and other data regarding medical images may be stored and automatically associated with other medical data (e.g., either earlier or later medical images). Additionally, such measurement data may be recorded so that it can be used in one or more disease stage assessment models (or simply "assessment models") that are used to analyze changes to one or more lesions over time and provide disease stage and/or progression information.

The menu 306 may be displayed automatically after a user provides an annotation and/or measurement. Alternatively, the menu 306 may be displayed in response to a command from any user controlled input device (e.g., keyboard, mouse, touchpad, microphone, etc.). In the example of FIG. 4, the menu 306 is provided in response to a right click of a mouse while the cursor is positioned over the annotation. The menu 306 allows the user to record annotation data, copy this exam's annotation data, copy all annotation data (e.g. copy the annotation data for more than one displayed image), show annotation data (see FIG. 8, for example), or enter a state where the labeling dialog shown in FIG. 5 (discussed below) always appears in response to a measurement, arrow annotation, and/or other specified annotation.

FIG. 5 is a sample user interface 500 that may be used by the viewer to index the tumor that was annotated in FIGS. 3-4 through the selection of various descriptive terms. In one embodiment, the annotation module of the computing system 150 allows the viewer to easily create associations between the same lesion in multiple exams, as well as to provide descriptive information regarding the lesion in each of the multiple exams. In the example user interface 500, which may be automatically displayed after a measurement (e.g., a bilinear measurement) is performed, the viewer can select an available index number to assign to the measured lesion. The computing system 150 may, by default, automatically assign a measurement to a next available index number, which may be adjusted by the viewer. For example, if no lesions have been previously measured, the computing system 150 may assign the measurement to "index lesion #1". However, if multiple lesions had been measured in a previous exam (and already assigned to index numbers), the viewer may change the assignment of the lesion to the appropriate index number (e.g., to index lesion #3 to align with measurements of the same lesion in a previous exam that were assigned to index lesion #3).

By associating the lesion measurements with particular index numbers, all measurements (and/or other data) of the lesions, across multiple exams, image series, modalities, etc., may be easily retrieved and analyzed. For example, information regarding a particular index lesion recorded in a current medical image, as well as multiple previous medical images, may be automatically included in a report and/or displayed to the viewer while reviewing images of the current exam. In other embodiments, lesions are associated with identifiers other than index numbers, such as letters, icons, text, graphics, or any other items that can be associated with respective lesions across multiple exams. Thus, discussion herein of an index number includes other embodiments where other items are used to correlate information (e.g., annotations and/or measurements) to respective lesions across multiple images and/or exams.

In one embodiment, only viewers with certain security rights can create annotations in the manner described above. Depending on the embodiment, the annotation data may be stored in a data structure (e.g., with each of the details selected by the user coded for compact storage and easy searching) and made available to the user and/or other users when related exams are viewed. In one embodiment, images are automatically selected as key images and/or added to a montage for the exam in response to recordation of one or more annotations with the images.

In the embodiment of FIG. 5, the user interface 500 allows the user to provide details regarding the lesion associated with the current measurement. For example, the user may select details for each of various types of information regarding the annotation, such as a category, organ name, position, mass type, characteristic, histology, etc., associated with the lesion. In one embodiment, the details regarding the lesion (e.g. those available in the categories discussed above) may be provided by a standard lexicon, such as the SNOMED and/or RADLEX (RSNA) lexicons. In some embodiments, the user may customize the provided medical lexicon with terminology that may be specialized for the viewer's area of practice, for example. In one embodiment, only viewers with certain security rights can modify/add/delete the pre-stored terms from which the same or other users can select. With the use of a standard lexicon, annotations may be more easily and accurately compared across multiple viewers, medical practices, etc. In other embodiments, a similar user interface may include different types of information than are shown in FIG. 5.

In one embodiment, the user interface 500 is at least partially pre-populated by the computing system 150 with details selected based on information available to the computing system 150. For example, the computing system 150 may access the DICOM header information in order to determine an organ name and position associated with a medical image, and pre-populate the user interface 500 with that information. Additionally, the computing system 150 may determine other details of the medical image based on computer aided diagnostics, for example, and pre-populate those details in the user interface 500, while still allowing the user to adjust those details if incorrect.

In the embodiment of FIG. 5, the current annotation label that is based on the selected details is shown in the annotation label interface 520. In one embodiment, the annotation label shown in interface 520 is updated in real time as the user selects details regarding the various data types (e.g., category, organ name, position, mass type, characteristics, histology, etc.).

In one embodiment, annotation and measurement data may be accessed based on criteria other than just the index number, such as any one or more of the details discussed above. For example, a user may select all annotation and measurement data associated with the auditory internal canal, which may include multiple index lesions (or no index lesions) across multiple exams. In one embodiment, when a labeled measurement or annotation is created, it is automatically copied to the clipboard so that it can be pasted into a report (or elsewhere).

Figure 6:
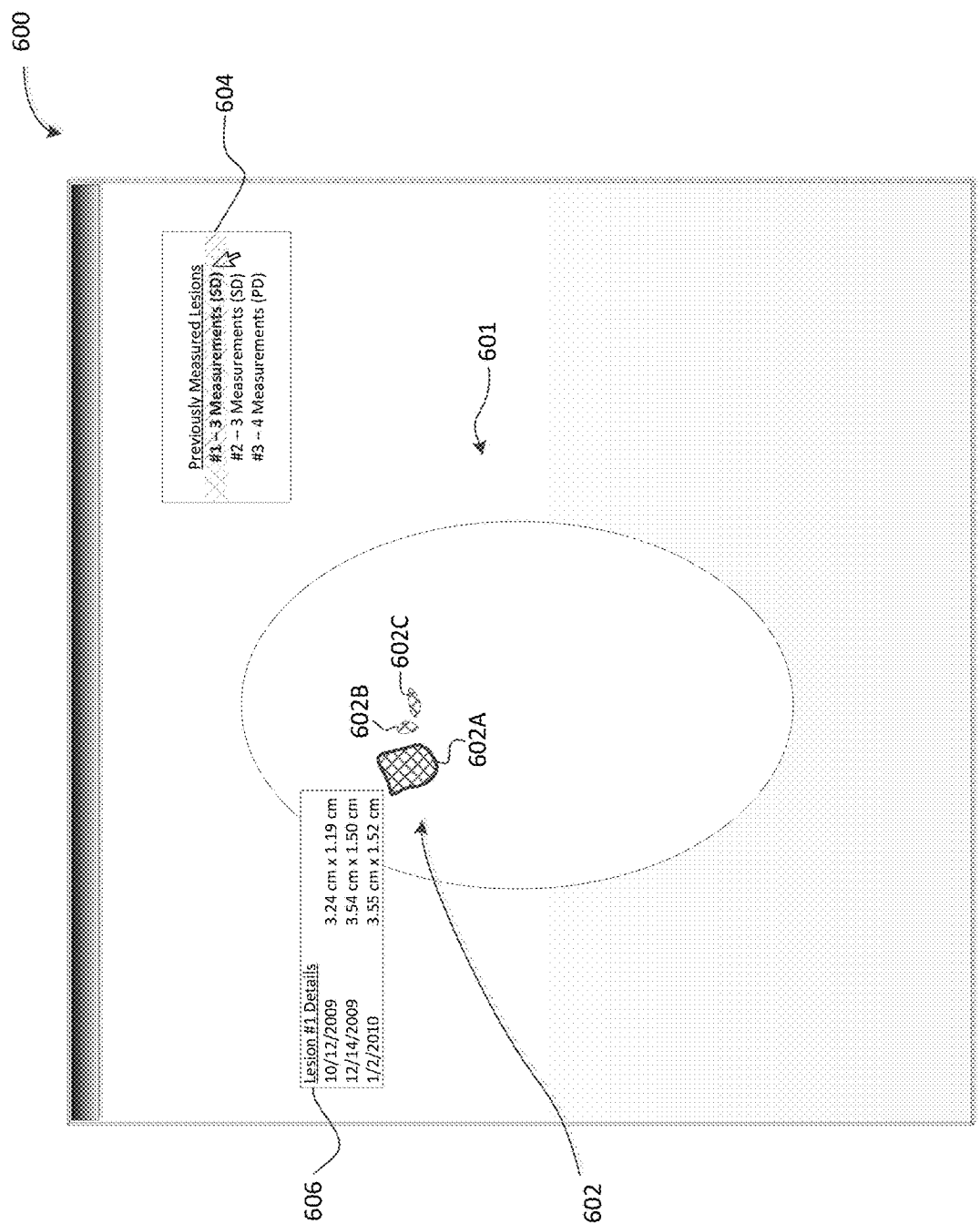
FIG. 6 is a sample user interface illustrating a representation of a medical image having multiple lesions, and a previously measured lesions table that allows the user to view previous measurements of each lesion.

FIG. 6 is a sample user interface 600 illustrating a representation of a medical image 601 having multiple lesions 602 (including lesions 602A, 602B, and 602C), and a previously measured lesions table 604 that allows the user to view previous measurements of each lesion. In the embodiment of FIG. 6, the user has hovered the cursor over index lesion #1 in the previously measured lesions table 604, which indicates that three previous measurements of index lesion #1 have been acquired. With the cursor hovering over index lesion #1 in the previously measured lesions table 604, the lesion details table 606 is displayed near lesion 602A, which has been classified as index lesion #1. Additionally, in this embodiment the index lesion #1 is highlighted so that the viewer can easily determine with which lesion the details are associated. Highlighting of the selected index lesion may be performed in any manner, such as adjusting display characteristics of the selected index lesion, outlining the index lesion, or in any other manner. Selection of a lesion for display of details may occur in response to any other predefined input.

In one embodiment, in response to opening of an image series the computing system 150 retrieves a list of measured lesions in the image series and/or previous related images series. A user interface that is populated with images associated with an index number and/or information regarding such images, may be provided to the user. Thus, the user can more easily organize review of new images based on the indexed lesions of the previous exams. For example, in addition to viewing a montage of a prior exam (e.g., with images that are automatically selected as key images based on the presence of annotations), the user can view the images with index lesions (as recorded in the prior exam) and know where to re-measure the index lesions in the current exam to provide the best comparison over time.

In the embodiment of FIG. 6, the index lesion #1 details 606 include three previous measurements of the specific index lesion. In one embodiment, the lesion details 606 are retrieved from a data structure that is updated by the annotation module discussed above with reference to FIG. 1. For example, when the viewer opens the image illustrated in FIG. 6, the system may automatically associate the image with images of previous exams of the same patient, and retrieve data regarding measurements performed on the previous exams. Thus, in one embodiment the information illustrated in FIG. 6 is provided to the viewer in response to simply opening the image. In other embodiments, the lesion details and/or the information regarding previously measured lesions in table 604 may be provided after the user measures the lesions shown in the current image and associates them with respective index lesions. For example, the user may measure the largest lesion 602A (e.g., using the bilateral measurement tool discussed above) and designate the lesion 602A as index lesion #1, such as by using a pop-up menu or a user interface similar to that of FIG. 5. In this embodiment, when the user designates the lesion 602A as index lesion #1, other information for the that lesion is retrieved and made available to the user, such as the previous measurements of the lesion from previous exams that is included in the lesion #1 details table 606.

In the example of FIG. 6, the index lesions shown in the previously measured lesions table 604 each have a disease stage indication, which is calculated based on at least the measurements from previously acquired images. In this example, index lesion #1 is indicated as "SD", which indicates that index lesion #1, taken alone, would be classified as a stable disease. Additionally, index lesion #3, which has had four previous measurements, is indicated as PD, which indicates that index lesion #3 would be classified as a progressive disease. Classifications of disease stages may be performed based on one or multiple assessment models, which are discussed in further detail below. Some assessment models may not provide separate disease classifications for individual lesions, but rather may provide only a single disease classification for an entire group of related lesions. Thus, in one embodiment each of the index lesions may not have a separate disease classification, but rather an overall disease classification determined based on measurements of each of the three index lesions may be provided.

Figure 7:
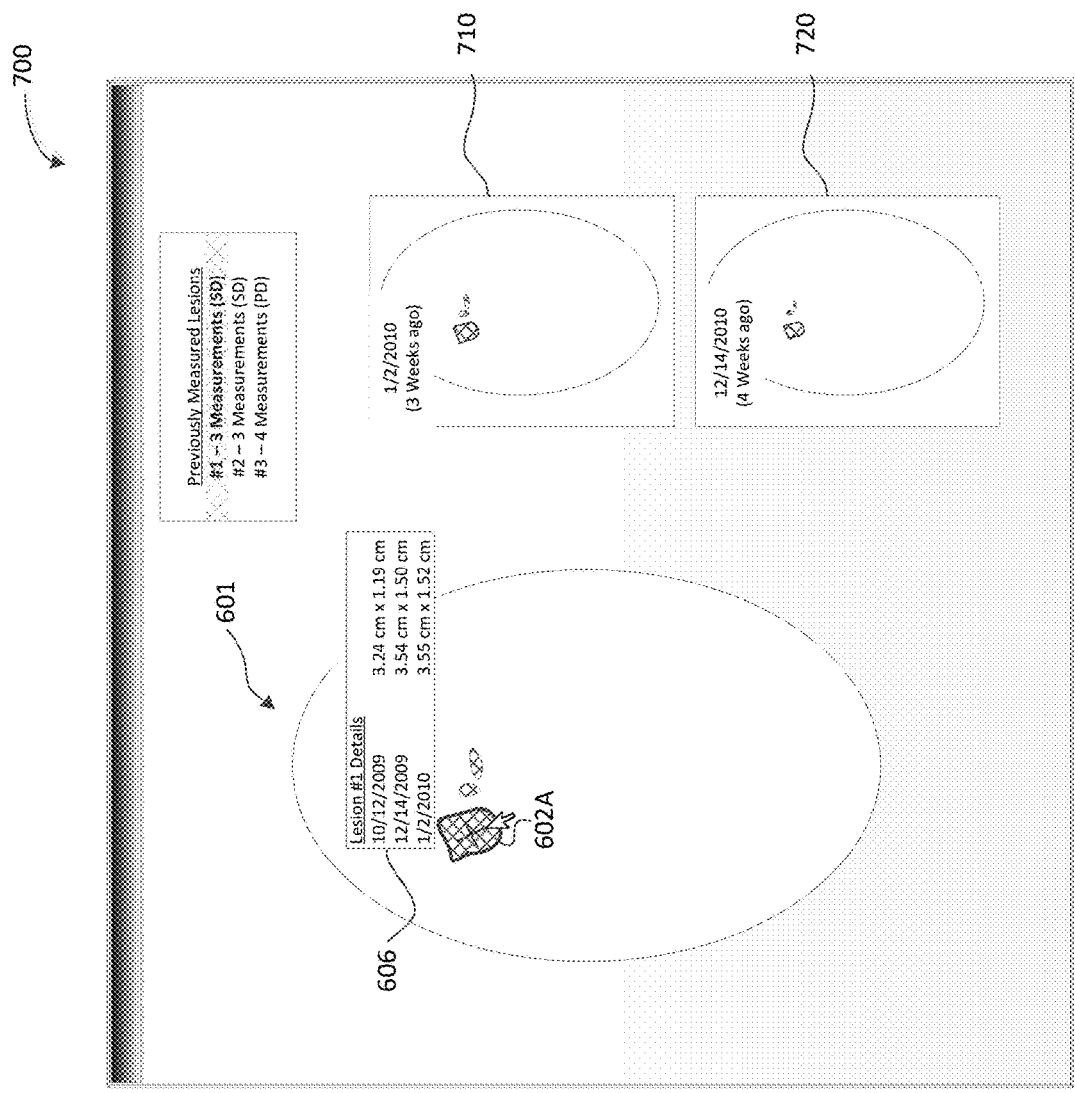
FIG. 7 is a sample user interface illustrating the same representation of a medical image as illustrated in FIG. 6, with lesion details displayed in response to movement of the cursor over a particular lesion.

FIG. 7 is a sample user interface 700 illustrating the same representation of a medical image 601 as illustrated in FIG. 6. In the embodiment of FIG. 7, the lesion details are displayed in response to movement of the cursor over a particular lesion. In the specific example of FIG. 7, the user has moved the mouse pointer over lesion 602A to cause the index lesion #1 details table 606 to appear. In some embodiments, the lesion details window 606 may be displayed in response to various actions of the user, such as selection of a particular lesion in a previously measured lesions table (e.g., as discussed with reference to FIG. 6), selection of a particular lesion (e.g., as shown with reference to FIG. 7), or in response to any other defined input from the user.

In the embodiment of FIG. 7, the user interface 700 also includes previous image panes 710 and 720 that include representations of related images, such as images from which the previous measurements of the selected index lesion were acquired. In this example, the index lesion 602A is selected and, in addition to details regarding previous measurements of that lesion being provided, user interfaces 710, 720, which include representations of actual images from the previous exams on which the measurements were taken for the selected lesion, are also displayed. In one embodiment, the previous image panes 710, 720 are provided automatically, in response to user preferences indicating that such previous image panes should be displayed when an index lesion with previous measurements is selected. In other embodiments, the previous image panes may be displayed in response to a user command when viewing the image 601.

In the embodiment of FIG. 7, the image panes 710, 720 also include the date of each of the previous measurements and an indication of how long ago each of the images was acquired (e.g., three weeks ago for the image of image pane 710 and four weeks ago for the image of image pane 720). The image panes may include additional or less data, such as the exact time of the image acquisition and/or reading of the images. The image panes may be configured so that the user can select displayed images in order to view a high-resolution version of the images and/or to compare one or more of the previous images with the current image, such as using the shuffling and interleaving techniques discussed in U.S. Pat. No. 7,885,440, issued on Feb. 8, 2011 and titled SYSTEMS AND METHODS FOR INTERLEAVING SERIES OF MEDICAL IMAGES, which is hereby incorporated by reference in its entirety.

Figure 8:
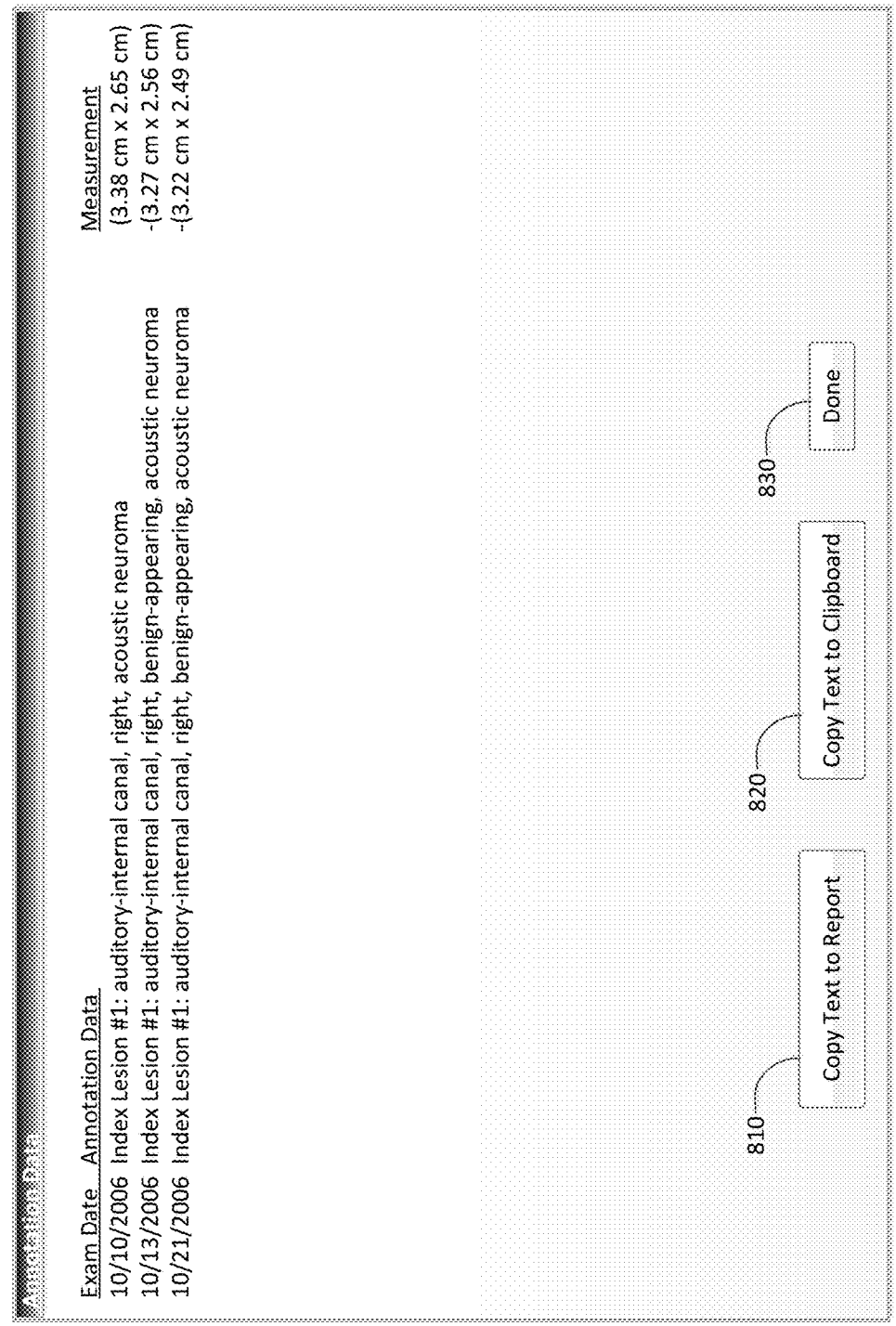
FIG. 8 is a sample user interface that provides detailed information regarding an index lesion across multiple exams.

FIG. 8 is a sample user interface 800 that provides detailed information regarding an index lesion across multiple exams. In this example, the information is provided in chronological order. The user interface 800 may be provided in response to any predefined user input, or may be automatically provided after certain actions are taken by the user, such as after a user marks an image as read or completes measurements of one or more lesions. In the embodiment of FIG. 8, the information regarding index lesion #1 is shown from each of three different exams. Additionally, information regarding the appearance of the lesion (which may be selected using a user interface such as that of FIG. 5) is also displayed along with the measurements of the lesion from each of the three exams.

In the embodiment of FIG. 8, the second and third measurements include an indication of change in the index lesion measurements when compared to the previous measurement. In this example, just prior to the measurement data for the Oct. 13, 2006 exam, a minus symbol is provided to indicate that the measurements of the Oct. 13, 2006 exam of index lesion #1 are smaller than previous measurements. Depending on the embodiment, the comparison may be based on an area calculation for the index lesion or may be based on other criteria, such as the length of the longest diameter from each of the measurements, the length of the short axis from each of the measurements, or some other combination of the measurements. In this example, a minus symbol is also provided next to the measurement for the Oct. 21, 2006 exam, indicating that the measurement of the index lesion #1 on Oct. 21, 2006 is smaller than the previous measurement. Depending on the embodiment, if multiple previous measurements are available, the comparison indicator may be with reference to the immediately prior exam, the oldest exam, or some combination of multiple prior exams. Additionally, other details regarding the measurements may be provided, such as is discussed in further detail below.

In the embodiment of FIG. 8, the user interface 800 also includes a copy text to report button 810, a copy text to clipboard button 820, and a done button 830. In this embodiment, the user may select the copy text to report button 810 to automatically place the displayed text into a report at the appropriate location within the report. In one embodiment, the user can select a portion of the displayed text prior to selecting the copy text report button 810 in order to copy only those portions selected. In one embodiment, the text is copied to the report document without the user needing to view the report document at the time of copying. Accordingly, the user can continue with other actions associated with the exam before ever seeing the report that includes the copied text. The copy text to clipboard button 820 similarly copies all of the displayed annotation data or a selected group of the annotation data so that the user can paste the data into another location, such as a report, at the user's convenience. The done button 820 returns the user to any previously viewed screen, or automatically advances the provided display to include a next image of an image series, for example.

Example Assessment Models

Figure 9:
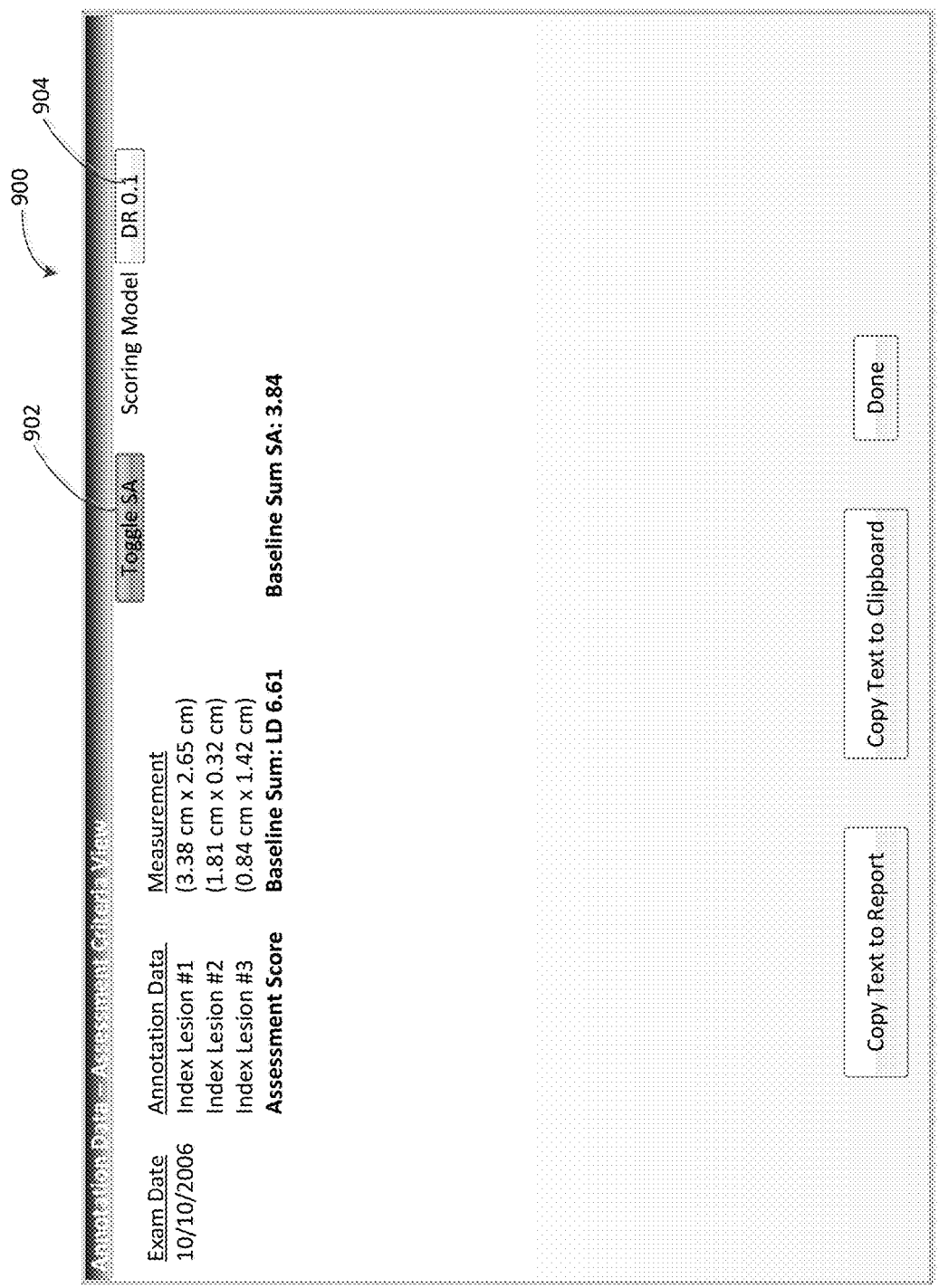
FIG. 9 is a sample user interface illustrating information regarding multiple lesions from a particular exam, and also including information regarding an assessment score.

FIG. 9 is a sample user interface 900 illustrating information regarding multiple lesions from a particular exam, and also including information regarding an assessment score. Various assessment models may be used to provide an easy to understand indication of a disease state (also referred to herein as disease stage, disease classification, or disease categorization), such as based on measurements of one or more lesions of the patient from one or more exams. For example, RECIST ("Response Evaluation Criteria In Solid Tumors") is an assessment model that defines when cancer patients improve ("respond"), stay the same ("stable") or worsen ("progression") during treatments. See, e.g., www.recist.com. RECIST uses measurements of lesions from multiple exams in order to determine the disease stage of a particular cancer. For example, RECIST sums a total of longest diameter measurements across the related lesions (certain lesions may not be of an appropriate size to be included in the calculation), such as all lesions associated with cancer in a particular organ, and compares the longest diameter sum with a longest diameter sum of a previous exam of the patient. The comparison of the longest diameter sums may then be used to determine a disease stage for the patient. For certain types of cancers, RECIST indicates that sums of the short axis measurements of lesions are used in order to determine the disease stage, rather than the longest diameter measurements. RECIST has multiple versions each with rules for which lesions qualify for measurement, how the measurements are combined, which previous exam is classified as the comparison exam, etc. In one embodiment of RECIST, the following disease stages may be determined based on measurement data:

Complete Response (CR): Disappearance of all target lesions

Partial Response (PR): At least a 30% decrease in the sum of the longest diameter of target lesions Stable Disease (SD): Neither sufficient shrinkage to qualify for PR nor sufficient increase to qualify for PD Progressive Disease (PD): At least a 20% increase in the sum of the longest diameter of target lesions.

Other assessment models include those being developed by Dr. Ronald Gottlieb, clinical professor of radiology at Arizona Cancer Center of the University of Arizona. Gottlieb's assessment model provides "a simplified quantitative visual scoring system to code CT imaging findings on radiology reports. A score of 1 was assigned if a tumor or lesion increased in size, a score of 0 represents no change, and a score of −1 represents a decrease in size. If new tumors appeared, the number of organs involved was numerically noted. All numbers were summed, and changes were noted compared to prior studies." See, SIIM: Visual-based tumor scoring system is better than RECIST, downloaded on Nov. 13, 2011 http://www.auntminnie.com/index.asp?sec=ser&sub=def&pag=dis&ItemID=95441. Thus, the Gottlieb assessment model, which includes its own rules for tumor measurement, scoring, and classification, is much different than the RECIST assessment model. Other assessment models may also be available. For example, assessment models that use other measurements, such as volume, area, contrast uptake, standard uptake value (e.g., SUV for PET and PET/CT) may also be used with the systems and methods discussed herein. For purposes of discussion, additional assessment models referred to as "DR" assessment models, in addition to the RECIST and Gottlieb assessment models, are discussed herein. The details of these assessment models, as disclosed in the above noted references and other publicly available documents, are incorporated by reference in their entirety.

Application of an assessment model is burdensome as the viewer first needs to understand the extensive rules for use of the assessment model and then needs to be able to retrieve the relevant lesion measurements, classify the lesion measurements (e.g. according to the specific assessment model being applied), and use the lesion measurements and/or classifications to develop the respective disease state. This burden is increased if multiple assessment models are applied. Accordingly, the systems and methods described herein disclose automation of application of one or more assessment models to quickly and easily assess disease stages for patients. For example, a viewer, who may be partially or entirely unfamiliar with the specific criteria for assessment models, may select one or more assessment models to be applied to lesion measurements of a patient, and the computing system 150 may automatically apply those selected assessment models in order to provide current, and possibly real-time, disease staging according to each of the one or more selected assessment models. Thus, the viewer is not required to stay current with all of the assessment models and the rules for each of the assessment models in order to make use of the potentially valuable disease classification information provided by the assessment models. In one embodiment, the assessment module of the software modules 151 periodically receives updates to assessment model rules so that the viewer is always provided with current disease staging based on the latest assessment models. Such updates may be provided in a push or pull architecture.

Returning to FIG. 9, the user interface 900 displays measurements for three index lesions from a particular exam. The user interface provides a longest diameter assessment score (e.g., the sum of the longest diameters using certain assessment models), as well as a short axis assessment score (e.g., the sum of the short axes using certain assessment models) for this exam. In this embodiment, the user may determine whether short axis information is provided by selecting the Toggle SA button 902. Thus, in this embodiment the short axis information may be removed by selecting the button 902. In other embodiments, controls may be provided to allow display of only the short axis information.

In this example, the longest diameter assessment score provides a baseline assessment score that is compared to later longest diameter assessment scores in order to determine a disease stage. Depending on the assessment model, the baseline assessment score may change over time. For example, once treatment (e.g., chemotherapy, radiation, etc.) has started, measurements associated with the next exam may provide the baseline assessment scores for future disease staging. In other assessment models, the assessment scores from the first exam in which one or more of the lesions were measured provide the baseline assessment scores. In other assessment models, assessment scores from other exams may be used as baseline assessment scores.

In the embodiment of FIG. 9, an assessment model selection interface 904 allows the user to select one or more of several available assessment models. As noted above, the underlying rules for the assessment models may be automatically updated and applied by the computing system 150. In one embodiment, the computing system 150 selects the appropriate assessment model based on user preferences, user group preferences, system preferences, and/or default software preferences, based on one or more of various types of information. For example, the computing system 150 may select one or more assessment models to apply to a particular image (or image series) based on user rules, site rules, tumor type, patient information, whether or not the patient is part of a clinical trial, treatment course, referring physician, etc.

Certain assessment model rules may indicate a minimum and/or maximum number of measurements that are used in calculation of assessment scores. In such an embodiment, the computing system 150 may indicate this information to the user and/or guide the user to measure the right number of lesions. Additionally, certain assessment model rules may require minimum dimension(s) for a measurement to be included in an assessment score. In such an embodiment, the computing system 150 may provide a popup (or other visual or audible notification) indicating that a current measurement does not qualify for measurement using one or more of the currently selected assessment models. The popup may further provide criteria for which lesions are considered to be measurable under the current assessment models (and possibly a subset of rules of the assessment model selected based on characteristics of the image, patient, referring physician, etc.).

Figure 10:
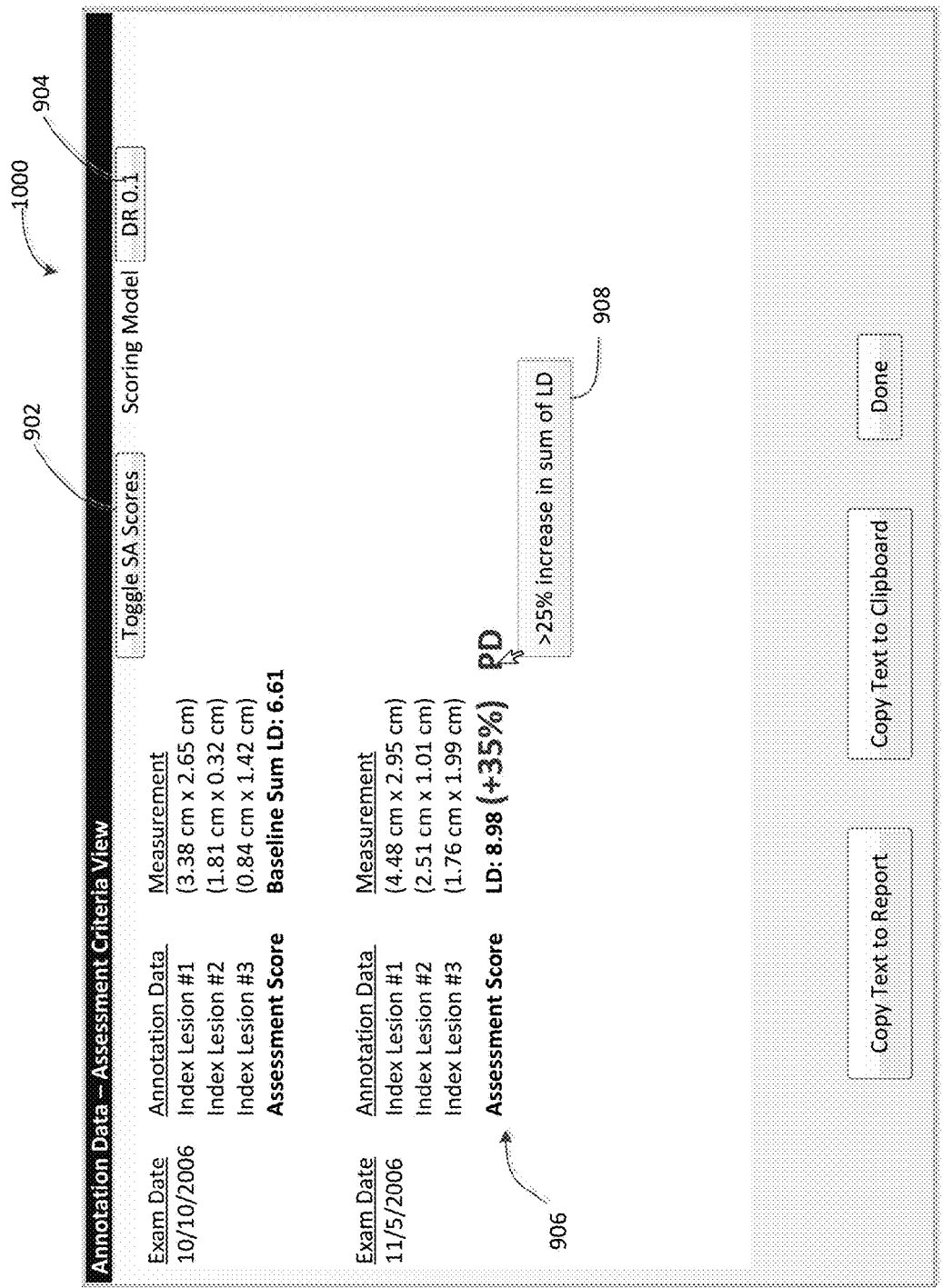
FIG. 10 is a sample user interface that provides information regarding multiple lesions at each of two different exams.

FIG. 10 is a sample user interface 1000 that provides information regarding multiple lesions at each of two different exams. In this example, an assessment model has been selected (DR 0.1) using the assessment model selection interface 904, and the assessment scores from each of two exams have been generated by the computing system 150 and used to determine a disease stage for the patient. In the example of FIG. 10, the disease stage is indicated as progressive (PD), because the increase in the longest diameter assessment score is more than a threshold for progressive disease classification according to the selected DR 0.1 assessment model. More particularly, the computing system 150 may compare the current longest diameter assessment score of the latest exam (8.98) to the baseline longest diameter assessment score (6.61) in order to determine that the assessment score has increased by 35%. Assuming the DR 0.1 assessment model classifies a disease stage as progressive if the increase in longest diameter assessment scores is more than 25%, the computing system 150 determines that the current disease stage is progressive and indicates such with the notation "PD" shown in FIG. 10.

In this embodiment, information regarding the particular rule of the assessment model that was applied to arrive at the disease stage may be provided in a pop-up window 908 in response to hovering the cursor over the scoring information 906 (or other user input). For example, in the embodiment of FIG. 10, the pop-up window 908 indicates that the PD disease stage was selected because, according to the DR 0.1 assessment model, there was ">25% increase in sum of LD." In one embodiment, further information regarding the assessment model, and more particularly, the application of the assessment model to arrive at the provided disease stage, may be displayed in response to a predefined user input, such as the user clicking on the displayed disease stage. Thus, in one embodiment basic information regarding the assessment model may be provided in response to hovering a cursor over the assessment information 906, while more detailed information may be provided in response to clicking (or otherwise selecting), the assessment information 906.

In one embodiment, the assessment models may have different rules for different disease types, disease areas, and/or other characteristics of the disease or patient. For example, an assessment model may have a first set of rules for solid tumor assessments (e.g. assessment scores may be based on the longest diameters of the lesions) and a second set of rules for lymph node assessments (e.g., assessment scores may be based on the short axis of the lesions). In one embodiment, the computing system 150 determines which rule set of a particular assessment model to apply based on information in the image header (e.g., the DICOM header) and/or information provided by the user (e.g., details provided using an interface such as user interface 500 in FIG. 5). For example, if a measurement is associated with a lymph node (e.g., based on DICOM header information of the image), the computing system 150 may select the appropriate rules for categorizing lymph node diseases using the selected assessment model. In one embodiment, if the computing system 150 cannot determine which set of rules to use within a particular assessment model, the computing system 150 may request information from the user regarding the proper rule set to apply.

Figure 11:
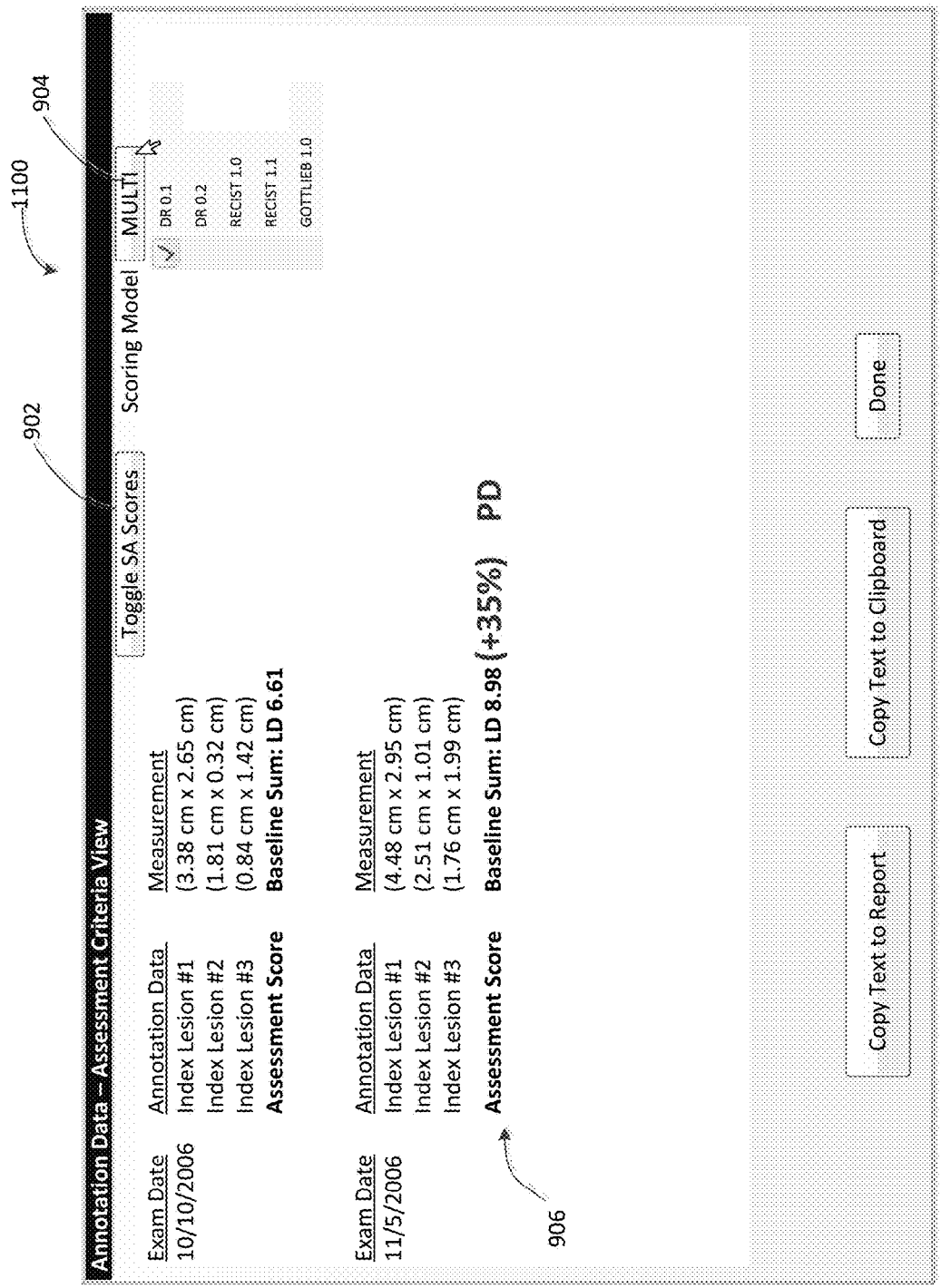
FIG. 11 is a sample user interface where the assessment model selection tool has been selected such that the user can indicate one or more assessment models to be applied to the particular examination data.

FIG. 11 is a sample user interface 1100 that includes much of the same information as in FIG. 10, with the model selection interface 904 selected. With the model selection interface 904 selected, the user can indicate one or more assessment models to be applied to the measurement data of the multiple exams.

Figure 12:
FIG. 12 is a sample user interface that includes much of the same information as the user interface of FIG. 11, with multiple assessment models selected.

FIG. 12 is a sample user interface 1200 that includes much of the same information as user interface 1100 of FIG. 11, with multiple assessment models selected. In particular, the example user interface 1200 illustrates that three different assessment models have been selected, namely, DR 0.1, DR 0.2, and RECIST 1.1. With these three assessment models selected, the assessment score information 906 is updated to include disease classification information for each of the three selected assessment models. Thus, the user has access to staging information from multiple assessment models. In this embodiment, additional details regarding one or more rules applied by respective assessment models in order to arrive at the illustrated disease stage are provided when the cursor is positioned over the respective assessment model information.

Figure 13:
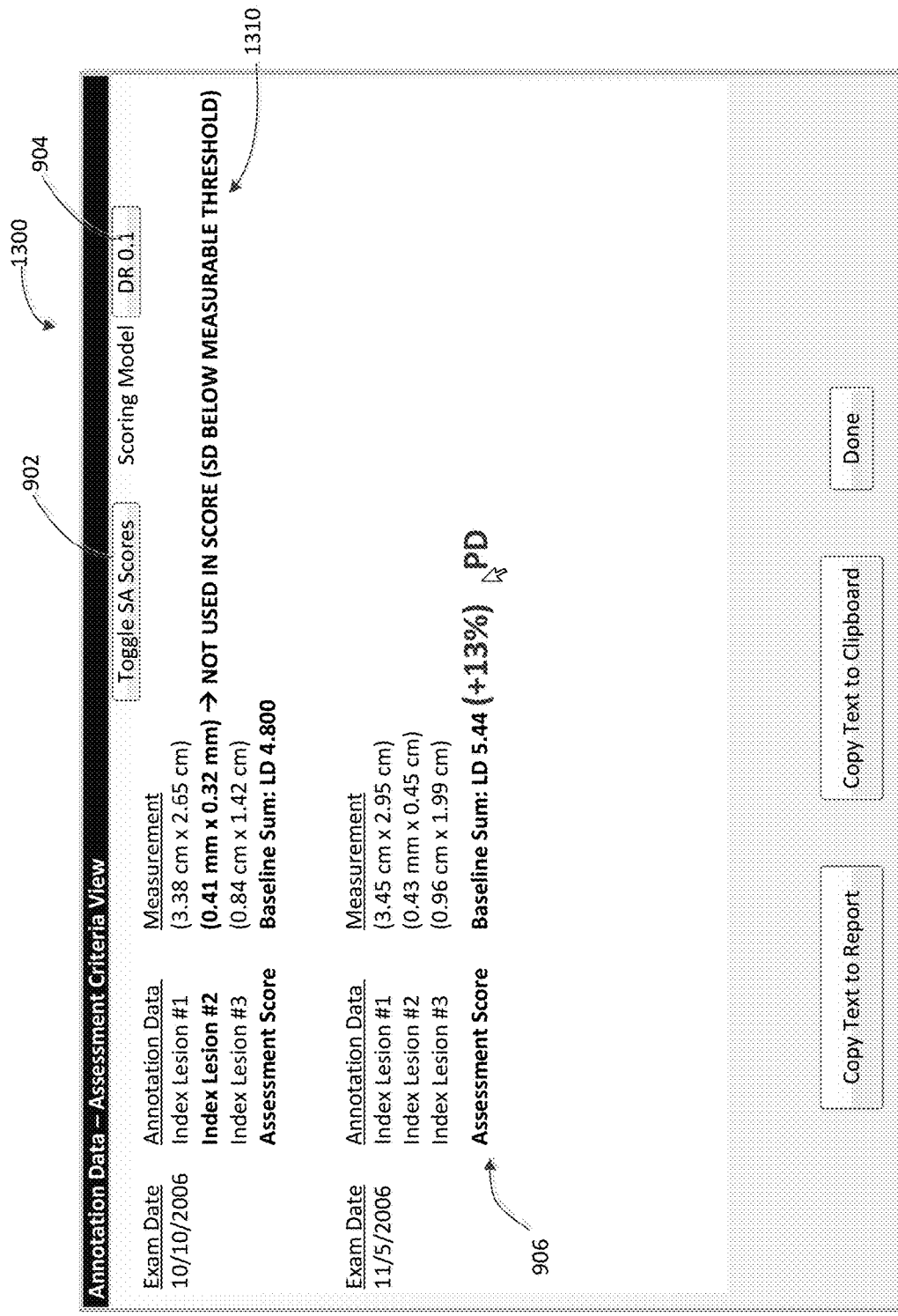
FIG. 13 illustrates a sample user interface that includes information regarding multiple lesion measurements from each of multiple exams.

FIG. 13 illustrates a sample user interface 1300 that includes information regarding multiple lesion measurements from each of multiple exams. In this embodiment, a warning 1310 is provided to the viewer that a particular measurement is not used in the assessment score in view of one or more rules of the selected assessment model. In this example, the short axis of the index lesion #2 is shorter than a measurable threshold for the DR 0.1 assessment model. Thus, the assessment model is used to determine which of multiple measurements are usable in generating assessment scores. In one embodiment, information regarding a rule that excludes a particular measurement may be provided in a pop-up window, for example, when the cursor hovers over the measurement. For example, the measurable short dimension threshold may be indicated when a cursor is hovered over the excluded index lesion #2 information for the Oct. 10, 2006 exam.

In one embodiment, the user interface 1300 (or other user interfaces discussed herein) may be displayed concurrently with images of one or more of the exams and, furthermore, may be updated in real time as measurements are acquired. In one embodiment, information regarding usable measurements, such as the warning 1310, may be provided as the user makes measurements on the medical image. Thus, a user may know immediately whether a measurement is usable in the one or more selected assessment models. In one embodiment, the measuring tool changes a display characteristic when the measurement is within a range that is usable in developing an assessment score. For example, a color of the bilinear measurement tool may change from red to green as the axes of the tool are adjusted within a range of dimensions that are usable by the selected assessment model. The color may change back to red if the axes are adjusted beyond a maximum dimension for the selected assessment model. Other colors, display characteristics, audible alerts, or other indicia of usable measurements may be provided as the user makes measurements on a medical image.

Depending on the embodiment, the user may have the ability to override certain rules of an assessment model in order to have an adjusted or modified disease staging calculated. For example, a user may override the exclusion of the index lesion #2 measurements from Oct. 10, 2006 by providing a predefined user input, such as by selecting an option on a menu to override the exclusion. If such an override is provided by the user, the disease stage may be displayed in a different manner that clearly indicates that the disease stage is based on modified rules and not strictly the indicated assessment model.

Figure 14:
FIG. 14 is a sample user interface that includes the same measurements as FIG. 13, but with a different assessment model applied.

FIG. 14 is a sample user interface 1400 that includes the same measurements as FIG. 13, but with a different assessment model applied. In particular, RECIST 1.1 assessment model has been selected and, based on the rules of RECIST 1.1, the measurements for index lesion #2 on Oct. 10, 2006 are included in the assessment score for that exam. With the inclusion of the index lesion #2 measurement in the Oct. 10, 2006 assessment score, and based on the RECIST 1.1 assessment model, the disease stage is indicated as stable (SD), whereas using the same exam data with the DR 0.1 assessment model, the disease stage is indicated in FIG. 13 as progressive (PD). Thus, disease staging may vary from one assessment model to the next.

FIG. 15 is a sample user interface 1500 that includes measurements for multiple index lesions at each of three different exam times. The user interface 1500 also includes a treatment data window 1510 that includes key information regarding treatments for the measured lesions. In one embodiment, the treatment data is chronological and is (horizontally) aligned with examination dates. Thus, in the embodiment of FIG. 15, the first treatment was Nov. 7, 2006, which is aligned slightly below the exam date Nov. 5, 2006. In other embodiments, different alignments of the treatment data are available. With the treatment data illustrated beside the exam data, the viewer can more easily correlate treatment with lesion measurements in determining how well a patient is responding to treatment.

As shown in FIG. 15, the disease classification for different exams is provided (e.g., according to the selected assessment model). In particular, a disease classification of progressive (PD) is provided after the Nov. 5, 2006 exam, while a disease classification of stable (SD) is provided after the Jan. 2, 2007 exam. As noted above, the baseline assessment score may vary between assessment models. In this embodiment, treatment dates are also illustrated as they may be used in determining baseline assessment scores for certain assessment models. For example, some assessment models may use the measurement data just prior to the beginning of treatment as the baseline for future assessment score. For example, based on the DR 0.1 assessment model that is selected in FIG. 15, the assessment score calculated in the Oct. 10, 2006 exam may be used as the baseline for calculating the disease stage after the Nov. 5, 2006 exam (which, in this case, indicates that the disease is progressive with a 35% increase in the longest diameter sums between the two exams). However, the baseline assessment score for purposes of calculating the disease stage after the Jan. 2, 2007 exam is the assessment score closest to the beginning of treatment. Depending on the assessment model, the exam closest to the beginning of treatment may be defined by a particular rule as an exam that is either before or after the first treatment date, may be limited to an exam that occurs after the initial treatment date, or may be limited to an exam that occurs before the initial treatment date. Additionally, some assessment models may update the baseline assessment score when different types of treatment begin, such as when radiation treatment begins after chemotherapy treatment has concluded. In some embodiments, multiple baseline assessment scores may be used in determining a current disease stage.

Figure 16:
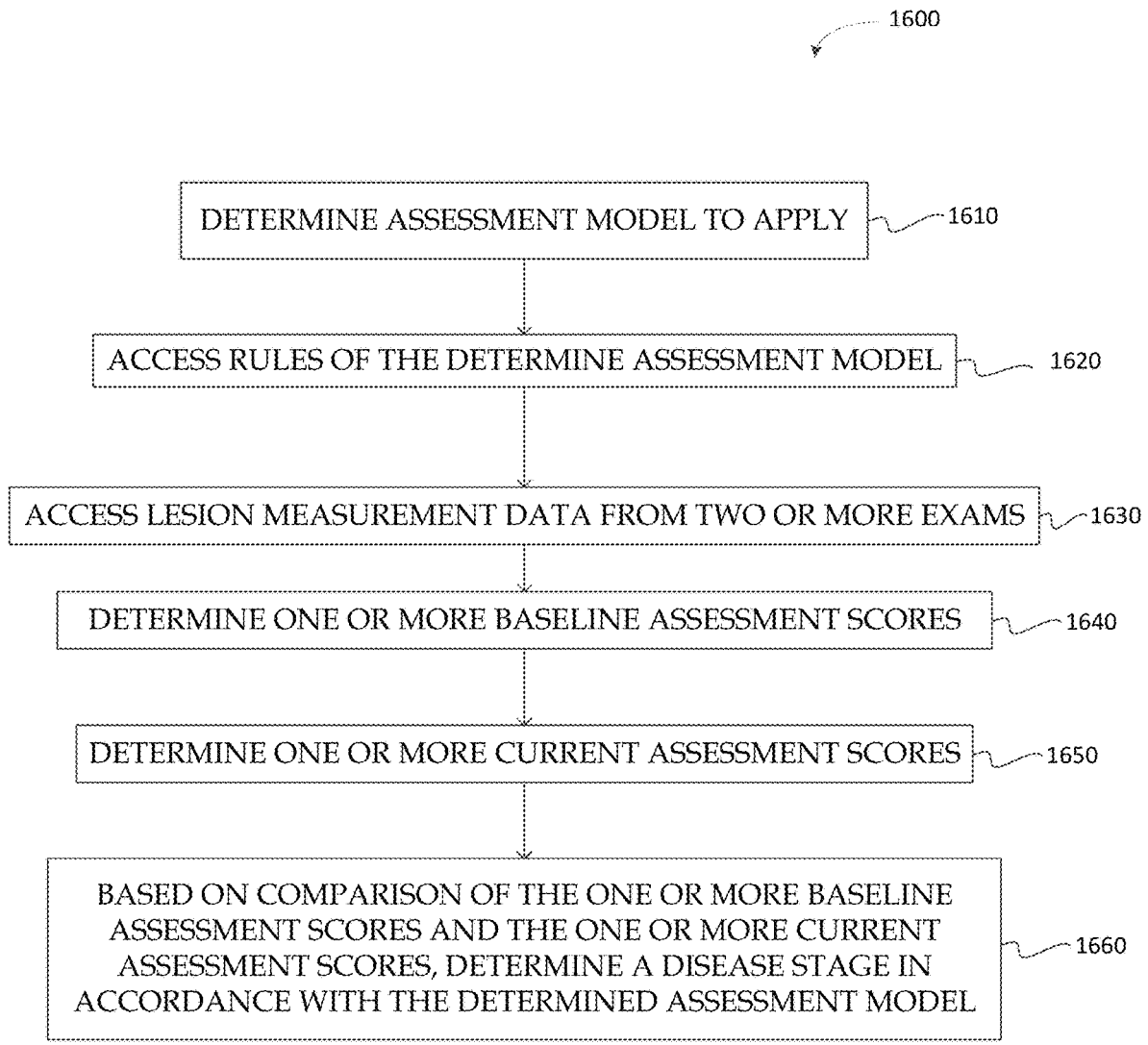
FIG. 16 is a flowchart illustrating one embodiment of a method of determining disease stage of a patient based on lesion measurements from multiple exams.

FIG. 16B is a flowchart illustrating one embodiment of a method of determining disease stage of a patient based on lesion measurements from multiple exams. Depending on the embodiment, the method of FIG. 16 may include fewer or additional blocks and/or the blocks may be performed in a different order than is illustrated. In one embodiment, the method of FIG. 16 is performed by the software modules 151 of the computing system 150 and, more particularly, by the assessment module. In other embodiments, the method may be performed by any other suitable computing device.

Beginning in block 1610, the computing system 150 determines an assessment model to apply. As discussed above, the assessment model may be selected automatically by the computing system (e.g., based on DICOM header information, information associated with previous exams of the patient, user preferences, site preferences, software preferences, etc. and/or manually by the viewer (e.g., using the assessment model selection interface 904 of FIG. 9).

Next, in block 1620, the computing system 150 determines rules of the assessment model to apply. Depending on the selected assessment model, one or multiple sets of rules may be available for determining disease states. As discussed above, the assessment module may be configured to determine the appropriate rules of a selected assessment model based on characteristics of the image, such as any data included in the DICOM header of the medical images. Alternatively, the computing system 150 may ask the user to select an appropriate rule set of the selected assessment model for application.

Moving to block 1630, lesion measurement data from two or more exams is accessed. As discussed above with reference to the bilinear measurement tool and the assessment module, measurements of lesions may be assigned to indexes that are used across multiple exams, image series, modalities, etc. Thus, the assessment module can access measurements of a particular lesion across multiple exams for comparison purposes. Similarly, the assessment module can access multiple lesion measurements from each of multiple exams for use in the selected assessment model.

In block 1640, the assessment module determines one or more baseline assessment scores, based on the lesion measurement data from the two or more exams. As discussed above, the exam or exams from which the baseline assessment score is determined may vary depending on the determined assessment model. Additionally, the exam and/or exams from which the baseline assessment score is determined may change as a patient undergoes treatment, for example.

Continuing to block 1650, the assessment module determines one or more current assessment scores, such as based on measurement data of a latest and/or current exam.

In block 1660, the assessment module determines a disease stage based on comparison of the one or more baseline assessment scores and the one or more current assessment scores. As noted above, the disease stage may be different depending on the determined assessment model and the rules of that determine assessment model. The determine disease stage may be provided in many different manners to the user, such as with an image display/measurement user interface, a reporting user interface, and/or transmission via an electronic communication (e.g., e-mail, SMS, etc.).

FIG. 17 is a sample report that includes annotations that were recorded while viewing images and were automatically included (or via a copy and paste by the user) into the report. In one embodiment, the computing system 150 processes the annotation data, including measurement data and assessment data, and extracts and/or generates information for inclusion in the report. The particular data that is provided in the report may be based on user preferences, user group preferences, system wide preferences, software preferences (e.g., preferences built into the modules), default preferences, or other customized preferences. For example, a particular user may wish to have only the textual annotation information included in the report, while other users may have both the textual annotation information and the measurement information included in the report.

SUMMARY

The methods and processes described above may be embodied in, and fully automated via, software code modules executed by one or more general purpose computers. The code modules may be stored in any type of computer-readable medium, such as a memory device (e.g., random access, flash memory, and the like), an optical medium (e.g., a CD, DVD, BluRay, and the like), or any other storage medium. Some or all of the methods may alternatively be embodied in specialized computer hardware.

The results of the disclosed methods may be stored in any type of computer data repository, such as relational databases and flat file systems that use magnetic disk storage and/or solid state RAM. The results of the disclosed methods and tasks may be persistently stored by transforming physical storage devices, such as solid state memory chips and/or magnetic disks, into a different state.

Alternate implementations are included within the scope of the embodiments described herein in which elements or functions may be deleted, executed out of order from that shown or discussed, including substantially concurrently (e.g., through multi-threaded processing, interrupt processing, or via multiple processors or processor cores) or in reverse order, depending on the functionality involved. Thus, in certain embodiments, not all described acts or events are necessary for the practice of the processes.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the logical blocks, modules, and processes illustrated may be made without departing from the spirit of the disclosure. As will be recognized, certain embodiments of the inventions described herein may be embodied within a form that does not provide all of the features and benefits set forth herein, as some features may be used or practiced separately from others.

What is claimed is:

1. A computing system comprising:
one or more hardware processors configured to execute software instructions to cause the computing system to:
automatically determine an assessment model from a plurality of available assessment models stored in computer memory to apply in determining a disease stage of a patient, wherein the assessment model is associated with one or more sets of assessment rules and, the plurality of available assessment models including the RECIST model and an additional assessment model different from the RECIST model;
select a first set of assessment rules from the one or more sets of assessment rules based on characteristics of at least one of a disease of the patient and the patient determined based on DICOM header information of a least one of a plurality of previous exams associated with the patient;
access, from the plurality of previous exams associated with the patient, previous lesion measurement data that satisfies the first set of assessment rules;
determine, according to the first set of assessment rules, a baseline assessment score based on the previous lesion measurement data;
determine, according to the first set of assessment rules, a current assessment score based on current lesion measurement data from a latest exam associated with the patient, wherein the latest exam associated with the patient was obtained after the plurality of previous exams associated with the patient, the current lesion measurement data generated using a software-implemented measurement tool movable on at least one image included in the latest exam associated with the patient to select at least one location within the at least one image for automatically determining the measurement data based on pixels included in the at least one image;
compare the baseline assessment score with the current assessment score in accordance with the determined assessment model;
determine and output a disease stage based on the comparison of the baseline assessment score with the current assessment score in accordance with the determined assessment model and the first set of assessment rules; and
in response to determining that at least one of a longest diameter or a short axis of a first lesion measurement of the previous lesion measurement data does not satisfy the first set of assessment rules, provide an audible or visual indication to a user, wherein the audible or visual indication comprises setting a color of at least a portion of the measurement tool displayed on a user interface to a first color, wherein the at least a portion of the measurement tool that is set to the first color comprises at least one of a first line segment or a second line segment that do not meet the first set of assessment rules.

2. The computing system of claim 1, wherein the one or more sets of assessment rules of the assessment model comprise at least the first set of assessment rules for use with a first category of lesions and a second set of assessment rules for use with a second category of lesions.

3. The computing system of claim 2, wherein the first category of lesions comprises solid tumors.

4. The computing system of claim 3, wherein the second category of lesions comprises lymph nodes.

5. The computing system of claim 1, wherein the first set of assessment rules specifies at least one of a minimum longest diameter or a minimum short axis for a lesion measurement to be used by the assessment model.

6. The computing system of claim 1, wherein determining the baseline assessment score comprises:
determining, from the previous lesion measurement data, a plurality of measurements of one or more lesions of a first previous exam of the plurality of previous exams;
for two or more of the plurality of measurements, determining respective longest diameters of the measurements;

summing up all the longest diameters of the measurements to determine a total of longest diameters of lesions in the first previous exam; and using the total of the longest diameters in the first previous exam as the baseline assessment score.

7. The computing system of claim 6, wherein determining the current assessment score comprises:

determining, from the current lesion measurement data, a second plurality of measurements of the one or more lesions of the latest exam;

for two or more of the second plurality of measurements, determining respective longest diameters of the second measurements;

summing up all of the longest diameters of the second measurements to determine a total of longest diameters of lesions in the latest exam; and using the total of the longest diameters in the latest exam as the current assessment score.

8. The computing system of claim 1, wherein determining the baseline assessment score comprises:

determining, from the previous lesions measurement data, a plurality of measurements of one or more lesions of a first previous exam of the plurality of previous exams;

for two or more of the plurality of measurements, determining respective short axis lengths of the measurements;

summing up all the short axis lengths of the measurements to determine a total of short axis lengths of lesions in the first previous exam; and using the total of the short axis lengths in the first previous exam as the baseline assessment score.

9. The computing system of claim 8, wherein determining the current assessment score comprises:

determining, from the current lesion measurement data, a second plurality of measurements of the one or more lesions of the latest exam;

for two or more of the second plurality of measurements, determining respective short axis lengths of the second measurements;

summing up all the short axis lengths of the second measurements to determine a total of short axis lengths of lesions in the latest exam; and using the total of the short axis lengths in the latest exam as the current assessment score.

10. The computing system of claim 1, wherein the one or more hardware processors are configured to execute software instructions to further cause the computing system to:

in response to an input from the user, override the first set of assessment rules to cause the computing system to use the first lesion measurement in determining the disease stage.

11. A computer-implemented method comprising:

by one or more processors executing program instructions:

automatically determining an assessment model from a plurality of available assessment models stored in computer memory to apply in determining a disease stage of a patient, the plurality of available assessment models including the RECIST model and the Gottlieb model;

selecting a first set of assessment rules from the one or more sets of assessment rules based on characteristics of at least one of a disease of the patient and the patient determined based on DICOM header information of at least one of a plurality of previous exams associated with the patient;

accessing, from the plurality of previous exams associated with the patient, previous lesion measurement data that satisfies the first set of assessment rules;

determining, according to the first set of assessment rules, a baseline assessment score based on the previous lesion measurement data;

determining, according to the first set of assessment rules, a current assessment score based on current lesion measurement data from a latest exam associated with the patient, wherein the latest exam associated with the patient was obtained after the plurality of previous exams associated with the patient, the current lesion measurement data generated using a software-implemented measurement tool movable on at least one image included in the latest exam associated with the patient to select at least one location within the at least one image for automatically determining the measurement data based on pixels included in the at least one image;

comparing the baseline assessment score with the current assessment score in accordance with the determined assessment model;

determining and outputting a disease stage based on the comparison of the baseline assessment score with the current assessment score in accordance with the determined assessment model and the first set of assessment rules; and in response to determining that at least one of a longest diameter or a short axis of a first lesion measurement of the previous lesion measurement data does not satisfy the first set of assessment rules, provide an audible or visual indication to a user, wherein the audible or visual indication comprises setting a color of at least a portion of the measurement tool displayed on a user interface to a first color, wherein the at least a portion of the measurement tool that is set to the first color comprises at least one of a first line segment or a second line segment that do not meet the first set of assessment rules.

12. The computer-implemented method of claim 11, wherein the first set of assessment rules specifies at least one of a minimum longest diameter or a minimum short axis for a lesion measurement to be used by the assessment model.

13. The computer-implemented method of claim 11, wherein determining the baseline assessment score comprises:

determining, from the previous lesion measurement data, a plurality of measurements of one or more lesions of a first previous exam of the plurality of previous exams;

for two or more of the plurality of measurements, determining respective longest diameters of the measurements;

summing up all the longest diameters of the measurements to determine a total of longest diameters of lesions in the first previous exam; and using the total of the longest diameters in the first previous exam as the baseline assessment score.

14. A computer-implemented method of claim 13, wherein determining the current assessment score comprises:

determining, from the current lesion measurement data, a second plurality of measurements of the one or more lesions of the latest exam;

for two or more of the second plurality of measurements, determining respective longest diameters of the second measurements;

summing up all the longest diameters of the second measurements to determine a total of longest diameters of lesions in the latest exam; and using the total of the longest diameters in the latest exam as the current assessment score.

15. The computer-implemented method of claim 11, wherein determining the baseline assessment score comprises:

determining, from the previous lesion measurement data, a plurality of measurements of one or more lesions of a first previous exam of the plurality of previous exams;

for two or more of the plurality of measurements, determining respective short axis lengths of the measurements;

summing up all the short axis lengths of the measurements to determine a total of short axis lengths of lesions in the first previous exam; and using the total of the short axis lengths in the first previous exam as the baseline assessment score.

16. The computer-implemented method of claim 15, wherein determining the current assessment score comprises:

determining, from the current lesion measurement data, a second plurality of measurements of the one or more lesions of the latest exam;

for two or more of the second plurality of measurements, determining respective short axis lengths of the second measurements;

summing up all the short axis lengths of the second measurements to determine a total of short axis lengths of lesions in the latest exam; and using the total of the short axis lengths in the latest exam as the current assessment score.

17. A system for determining a disease state of a lesion, the system comprising:

one or more hardware processors configured to execute software instructions to cause the system to:

receive, from a user, a selection of a plurality of assessment models to be applied to lesion measurements of a patient from a plurality of available assessment models stored in computer memory;

retrieving one or more assessment rules associated with each of the plurality of assessment models from the computer memory;

automatically receive an update to the one or more assessment rules of one of the plurality of assessment models via a push or a pull architecture;

apply the update to the one or more assessment rules;

automatically apply each of the plurality of assessment models to one or more of the lesion measurements of the patient to provide disease staging according to each of the plurality of assessment models;

provide the determined disease staging to the user via a user interface; and in response to determining that at least one of the one or more lesion measurements does not satisfy at least one of the one or more assessment rules, provide an audible or visual indication to a user, wherein the audible or visual indication comprises setting a color of at least a portion of a software-implemented measurement tool, movable on at least one image displayed on a user interface, to a first color, wherein the at least a portion of the measurement tool that is set to the first color comprises at least one of a first line segment or a second line segment that do not meet the first set of assessment rules.

* * * * *